(12) United States Patent
Zhang et al.

(10) Patent No.: US 10,561,332 B2
(45) Date of Patent: Feb. 18, 2020

(54) CARDIAC ELECTRICAL SIGNAL GROSS MORPHOLOGY-BASED NOISE DETECTION FOR REJECTION OF VENTRICULAR TACHYARRHYTHMIA DETECTION

(71) Applicant: Medtronic, Inc., Minneapolis, MN (US)

(72) Inventors: Xusheng Zhang, Shoreview, MN (US); Jian Cao, Shoreview, MN (US); Saul E. Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 15/653,969

(22) Filed: Jul. 19, 2017

(65) Prior Publication Data

US 2018/0028085 A1 Feb. 1, 2018

Related U.S. Application Data

(60) Provisional application No. 62/367,166, filed on Jul. 27, 2016.

(51) Int. Cl.
*A61B 5/0464* (2006.01)
*A61B 5/021* (2006.01)
(Continued)

(52) U.S. Cl.
CPC ........ *A61B 5/0464* (2013.01); *A61B 5/02108* (2013.01); *A61B 5/04012* (2013.01); *A61B 5/04017* (2013.01); *A61B 5/0452* (2013.01); *A61B 5/7203* (2013.01); *A61N 1/3925* (2013.01); *A61B 5/0245* (2013.01); *A61B 5/4836* (2013.01); *A61N 1/3704* (2013.01); *A61N 1/3956* (2013.01);
(Continued)

(58) Field of Classification Search
CPC ... A61B 5/0464; A61B 5/0456; A61B 5/7203; A61B 5/04011; A61B 5/01012; A61N 1/3621; A61N 1/365; A61N 1/3702
See application file for complete search history.

(56) References Cited

U.S. PATENT DOCUMENTS 5,354,316 A 10/1994 Keimel
5,545,186 A 8/1996 Olson et al.
(Continued)

FOREIGN PATENT DOCUMENTS

WO 2008137536 A1 11/2008

OTHER PUBLICATIONS (PCT/US2017/043828) PCT Notification of Transmittal of the International Search Report and the Written Opinion of the International Searching Authority, dated Nov. 3, 2017, 10 pages.
(Continued)

*Primary Examiner* — Tammie K Marlen

(57) ABSTRACT

A medical device system, such as an extra-cardiovascular implantable cardioverter defibrillator ICD, senses R-waves from a first cardiac electrical signal by a first sensing channel and stores a time segment of a second cardiac electrical signal in response to each sensed R-wave. The medical device system determines a morphology parameter correlated to signal noise from time segments of the second cardiac electrical signal, detects a noisy signal segment based on the signal morphology parameter; and withholds detection of a tachyarrhythmia episode in response to detecting a threshold number of noisy signal segments.

31 Claims, 21 Drawing Sheets

(51) Int. Cl.
    *A61B 5/04*           (2006.01)
    *A61B 5/00*           (2006.01)
    *A61N 1/39*           (2006.01)
    *A61B 5/0452*        (2006.01)
    *A61B 5/0245*        (2006.01)
    *A61N 1/37*           (2006.01)
    *H03H 21/00*        (2006.01)

(52) U.S. Cl.
    CPC .......... *A61N 1/3962* (2013.01); *A61N 1/3987* (2013.01); *H03H 21/0012* (2013.01)

(56) References Cited

U.S. PATENT DOCUMENTS

| | | | |
|---|---|---|---|
| 5,891,171 | A | 4/1999 | Wickham |
| 6,393,316 | B1 | 5/2002 | Gillberg et al. |
| 7,027,858 | B2 | 4/2006 | Cao et al. |
| 7,031,765 | B2 | 4/2006 | Ritscher et al. |
| 7,031,771 | B2 | 4/2006 | Brown et al. |
| 7,330,757 | B2 | 2/2008 | Ostroff et al. |
| 7,444,182 | B2 | 10/2008 | Ostroff et al. |
| 7,515,956 | B2 | 4/2009 | Thompson |
| 7,627,368 | B2 | 12/2009 | Houben et al. |
| 7,715,906 | B2 | 5/2010 | Krause et al. |
| 7,734,333 | B2 | 6/2010 | Ghanem et al. |
| 7,734,336 | B2 | 6/2010 | Ghanem et al. |
| 7,761,150 | B2 | 7/2010 | Ghanem et al. |
| 7,769,452 | B2 | 8/2010 | Ghanem et al. |
| 7,831,304 | B2 | 11/2010 | Cao et al. |
| 7,907,993 | B2 | 3/2011 | Ghanem et al. |
| 7,941,214 | B2 | 5/2011 | Kleckner et al. |
| 7,991,471 | B2 | 8/2011 | Ghanem et al. |
| 8,050,754 | B2 | 11/2011 | Ghanem et al. |
| 8,095,206 | B2 | 1/2012 | Ghanem et al. |
| 8,160,684 | B2 | 4/2012 | Ghanem et al. |
| 8,306,618 | B2 | 11/2012 | Ghanem et al. |
| 8,435,185 | B2 | 5/2013 | Ghanem et al. |
| 8,437,842 | B2 | 5/2013 | Ghanem et al. |
| 8,588,895 | B2 | 11/2013 | Sanghera et al. |
| 8,825,145 | B1 | 9/2014 | Zhang |
| 8,886,296 | B2 | 11/2014 | Patel |
| 8,914,106 | B2 | 12/2014 | Charlton et al. |
| 8,942,802 | B2 | 3/2015 | Sarkar et al. |
| 8,977,350 | B2 | 3/2015 | Sarkar et al. |
| 8,983,586 | B2 | 3/2015 | Zhang |
| 9,486,155 | B2 | 11/2016 | Sarkar et al. |
| 9,603,543 | B2 | 3/2017 | Sarkar et al. |
| 2007/0038253 | A1 | 2/2007 | Kim et al. |
| 2007/0232948 | A1 | 10/2007 | Stadler et al. |
| 2014/0323894 | A1 | 10/2014 | Zhang et al. |
| 2015/0273227 | A1 | 10/2015 | Zhang et al. |
| 2015/0305642 | A1 | 10/2015 | Reinke et al. |
| 2015/0306375 | A1 | 10/2015 | Marshall et al. |
| 2015/0306410 | A1 | 10/2015 | Marshall et al. |
| 2016/0022166 | A1 | 1/2016 | Stadler et al. |
| 2016/0051159 | A1 | 2/2016 | Mazaeva et al. |
| 2016/0106991 | A1 | 4/2016 | Stadler et al. |
| 2016/0158567 | A1 | 6/2016 | Marshall et al. |
| 2016/0235320 | A1 | 8/2016 | Sarkar et al. |
| 2016/0235321 | A1 | 8/2016 | Sarkar et al. |

OTHER PUBLICATIONS

Cao, et al., "Multi-Threshold Sensing of Cardiac Electrical Signals in an Extracardiovascular Implantable Cardioverter Defibrillator", filed Apr. 29, 2016, U.S. Appl. No. 15/142,171 71 pages.

Cao et al., "Cardiac Electrical Signal Morphology and Pattern-Based T-Wave Oversensing Rejection", filed Jul. 27, 2016, U.S. Appl. No. 62/367,221 92 pages.

Greenhut et al., "Cardiac Electrical Signal Noise Detection for Tachyarrhythmia Episode Rejection", filed May 26, 2017, U.S. Appl. No. 15/606,216 101 pages.

Swerdlow et al., "Advanced ICD Troubleshooting: Part 1", Pace, vol. 28, Dec. 2005, 25 pages.

Zhang et al., "System and Method for Sensing and Detection in an Extra-Cardiovascular Implantable Cardioverter Defibrillator", filed Apr. 28, 2016 77 pages.

CARDIAC ELECTRICAL SIGNAL GROSS MORPHOLOGY-BASED NOISE DETECTION FOR REJECTION OF VENTRICULAR TACHYARRHYTHMIA DETECTION

REFERENCE TO RELATED APPLICATION

This application claims the benefit of U.S. Patent Application No. 62/367,166, filed provisionally on Jul. 27, 2016, the entire content of which is incorporated herein by reference.

TECHNICAL FIELD

The disclosure relates generally to a medical device system and method for detecting noise in a cardiac electrical signal and withholding a ventricular tachyarrhythmia detection in response to detecting noise.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for detecting noise-contaminated cardiac electrical signal segments and reject a ventricular tachyarrhythmia detection in response to detecting noisy signal segments. A medical device system operating according to the techniques disclosed herein may determine signal morphology parameters for a cardiac electrical signal segment that extends beyond an expected QRS signal width for identifying noisy signal segments based on the morphology parameters.

In one example, the disclosure provides a medical device including a sensing circuit having a first sensing channel configured to receive a first cardiac electrical signal and sense R-waves in response to crossings of a sensing amplitude threshold by the first cardiac electrical signal and having a second sensing channel configured to receive a second cardiac electrical signal. The second sensing channel receives the second cardiac electrical signal via a sensing electrode vector and different than a sensing electrode vector used by the first sensing channel. The medical device further includes a memory and a control circuit coupled to the sensing circuit and the memory. The control circuit is configured to store a time segment of the second cardiac electrical signal in the memory for each of the plurality of R-waves sensed by the first sensing channel. The control circuit is configured to, for each of a plurality of the stored time segments, determine a morphology parameter correlated to signal noise from the stored time segment and detect the stored time segment as being a noisy signal segment based on the morphology parameter determined for the respective stored time segment. The control circuit withholds detection of a tachyarrhythmia episode in response to detecting at least a threshold number of the stored time segments as noisy signal segments.

In another example, the disclosure provides a method including sensing R-waves by a first sensing channel of a sensing circuit of a medical device in response to crossings of a sensing amplitude threshold by a first cardiac electrical signal, the first cardiac electrical signal received by the first sensing channel via a first sensing electrode vector coupled to the medical device; storing a time segment of a second cardiac electrical signal in a memory of the for each of the plurality of R-waves sensed by the first sensing channel, the second cardiac electrical signal received via a second sensing electrode vector coupled to the medical device and different than the first sensing electrode vector. The method further includes, for each of a plurality of the stored time segments, determining a morphology parameter correlated to signal noise from the stored time segment; detecting the stored time segment as being a noisy signal segment based on the morphology parameter determined for the respective stored time segment, and withholding detection of a tachyarrhythmia episode in response to detecting at least a threshold number of the stored time segments as noisy signal segments In another example, the disclosure provides a non-transitory, computer-readable storage medium comprising a set of instructions which, when executed by a control circuit of a medical device, cause the medical device to sense R-waves by a first sensing channel of a sensing circuit of the medical device in response to crossings of a sensing amplitude threshold by a first cardiac electrical signal, the first cardiac electrical signal received by the first sensing channel via a first sensing electrode vector coupled to the medical device; store a time segment of a second cardiac electrical signal in medical device memory in response to each one of the plurality of R-waves sensed by the first sensing channel, the second cardiac electrical signal received via a second sensing electrode vector by a second sensing channel of the medical device; for each one of a plurality of the stored time segments determine a morphology parameter correlated to signal noise from the stored time segment and detect the stored time segment as being a noisy signal segment based on the morphology parameter determined for the respective stored time segment; and withhold detection of a tachyarrhythmia episode in response to detecting at least a threshold number of the stored time segments as noisy signal segments.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting noise contamination of a cardiac electrical signal in a medical device system and withholding detection of a ventricular tachyarrhythmia in response to detecting noise. The medical device system may be any implantable or external medical device enabled for sensing cardiac electrical signals, including implantable pacemakers, implantable cardioverter-defibrillators (ICDs), cardiac resynchronization therapy (CRT) devices, or cardiac monitors coupled to extra-cardiovascular, transvenous, epicardial or intrapericardial leads carrying cardiac sensing electrodes; leadless pacemakers, ICDs or cardiac monitors having housing-based sensing electrodes; and external pacemakers, defibrillators, or cardiac monitors coupled to external, surface or skin electrodes.

However, the techniques are described in conjunction with an implantable medical lead carrying extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for detecting noisy signals acquired using extra-cardiovascular electrodes and withhold detection of ventricular tachycardia (VT) and ventricular fibrillation (VF) when signal noise is identified.

Figure 1A:
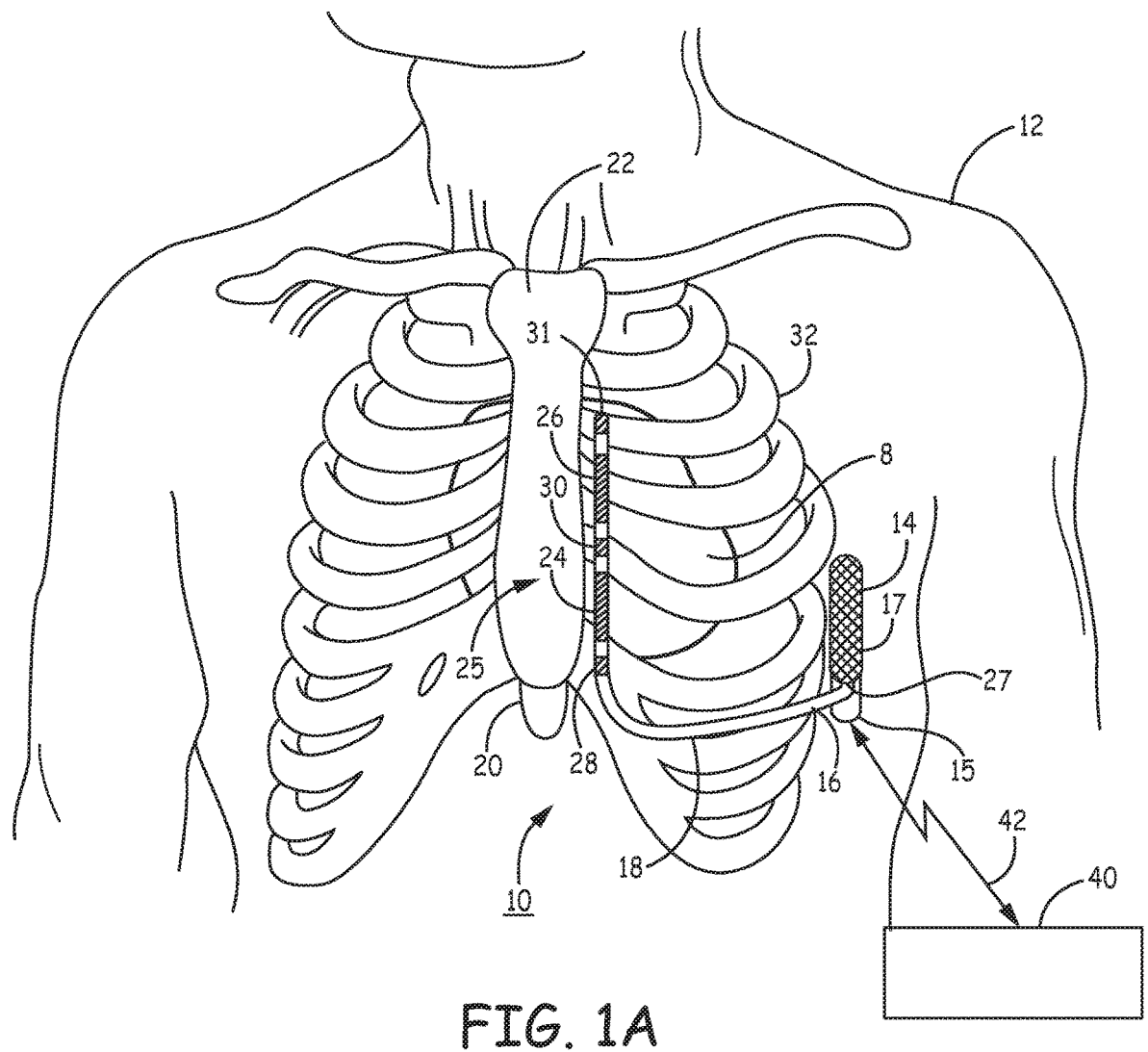
FIGS. 1A and 1B are conceptual diagrams of an extra-cardiovascular ICD system according to one example.
Figure 1B:
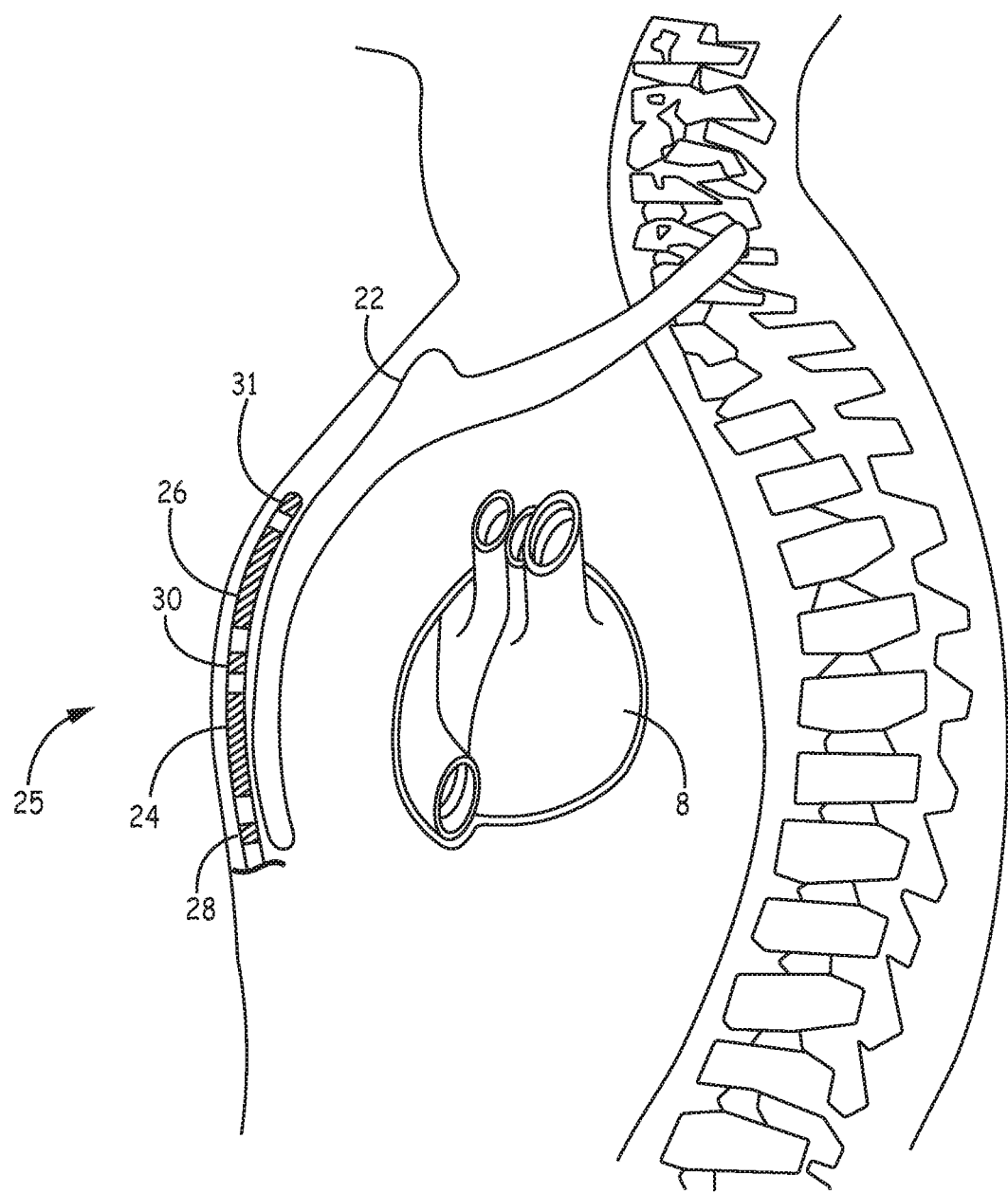

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a can electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a pacing electrode vector for delivering extra-cardiovascular pacing pulses such as ATP pulses and/or in a sensing vector used to sense cardiac electrical signals and detect VT and VF.

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31, which may be separate respective insulated conductors within the lead body. The respective conductors electrically couple the electrodes 24, 26, 28, 30 and 31 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, VT or VF. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30 and between one of pace/sense electrodes 28 or 30 and housing 15, and ATP pulses are delivered between pace/sense electrode 30 used as a cathode electrode and defibrillation electrode 24 used as a return anode electrode. In other examples, pacing pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and pacing electrode vectors may be selected according to individual patient need.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program R-wave sensing parameters, cardiac rhythm detection parameters and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
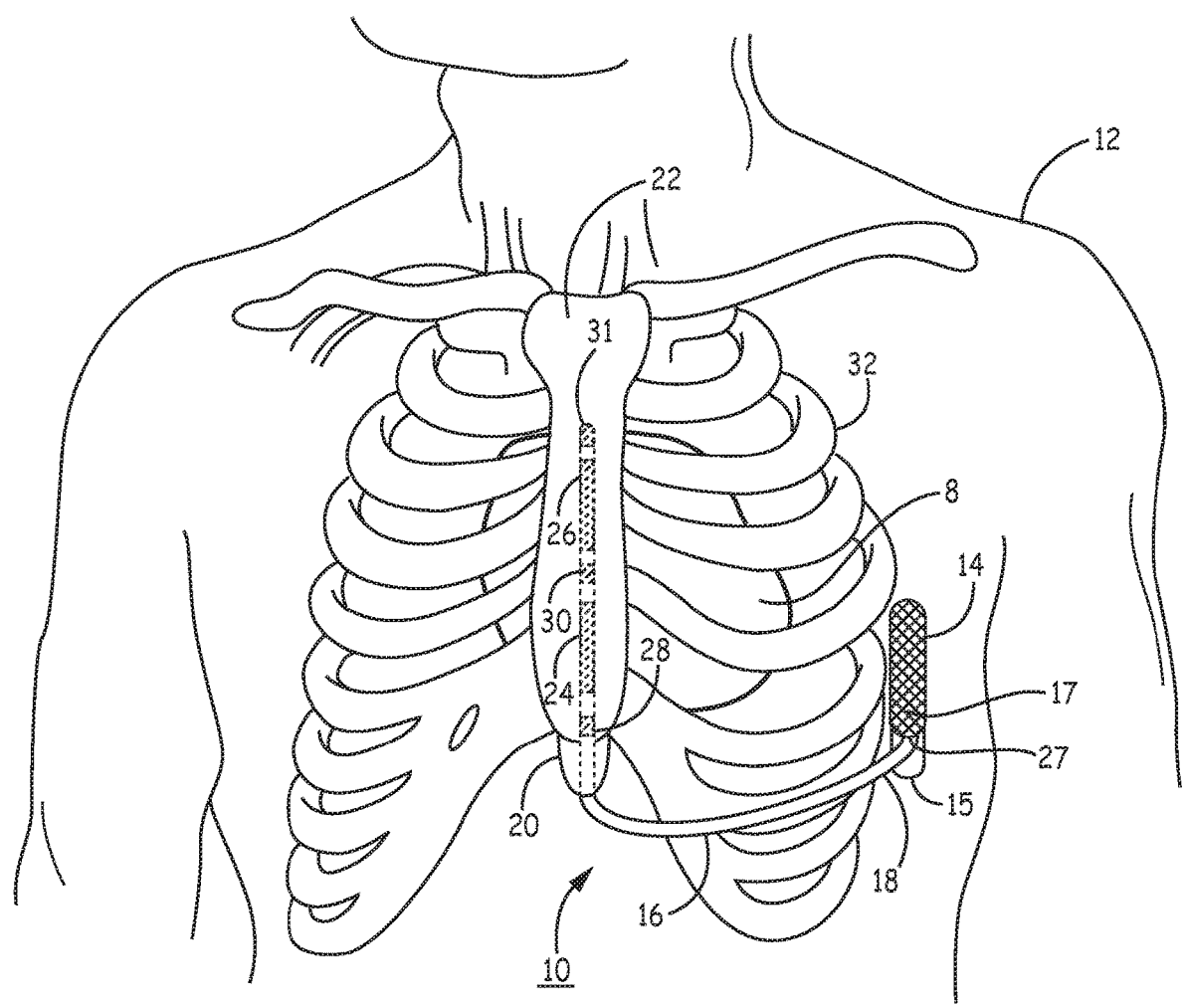
FIGS. 2A-2C are conceptual diagrams of a patient implanted with the extra-cardiovascular ICD system of FIG. 1A in a different implant configuration.
Figure 2B:
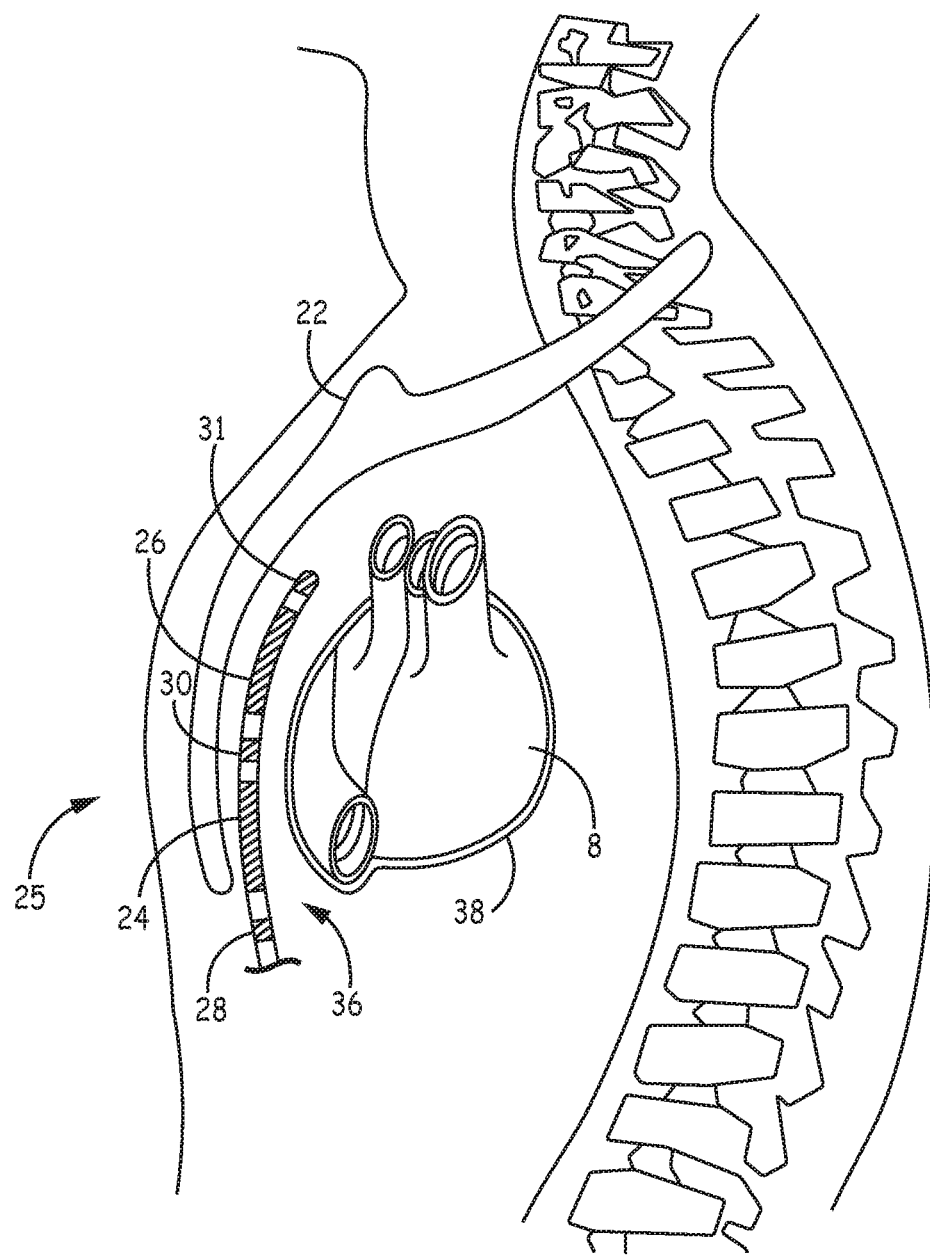
Figure 2C:
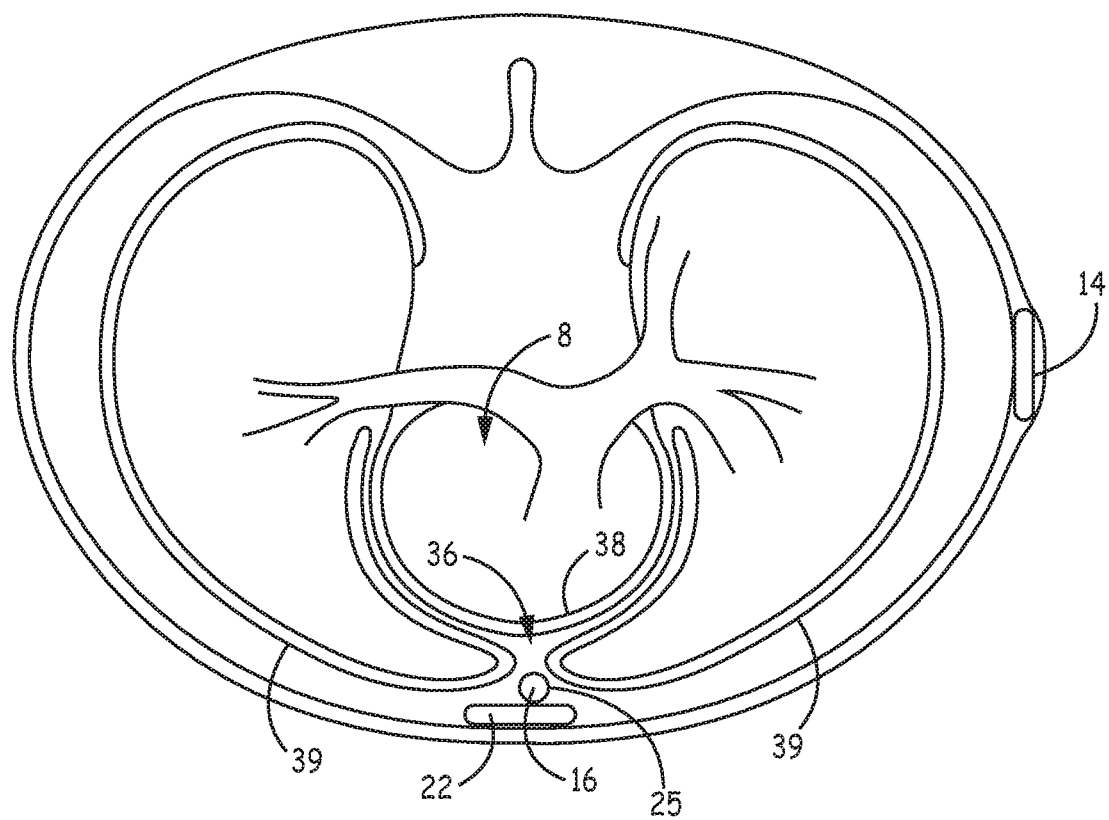

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the cardiac pacing techniques described herein are generally disclosed in the above-incorporated patent applications.

Figure 3:
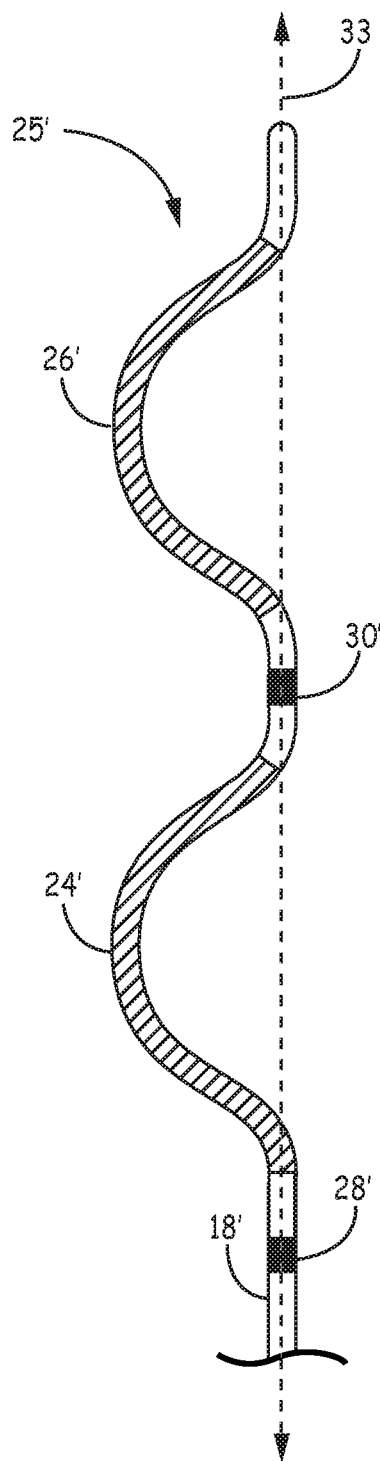
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε" Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. Pat. Publication No. 2016/0158567 (Marshall, et al.), incorporated herein by reference in its entirety.

Figure 4:
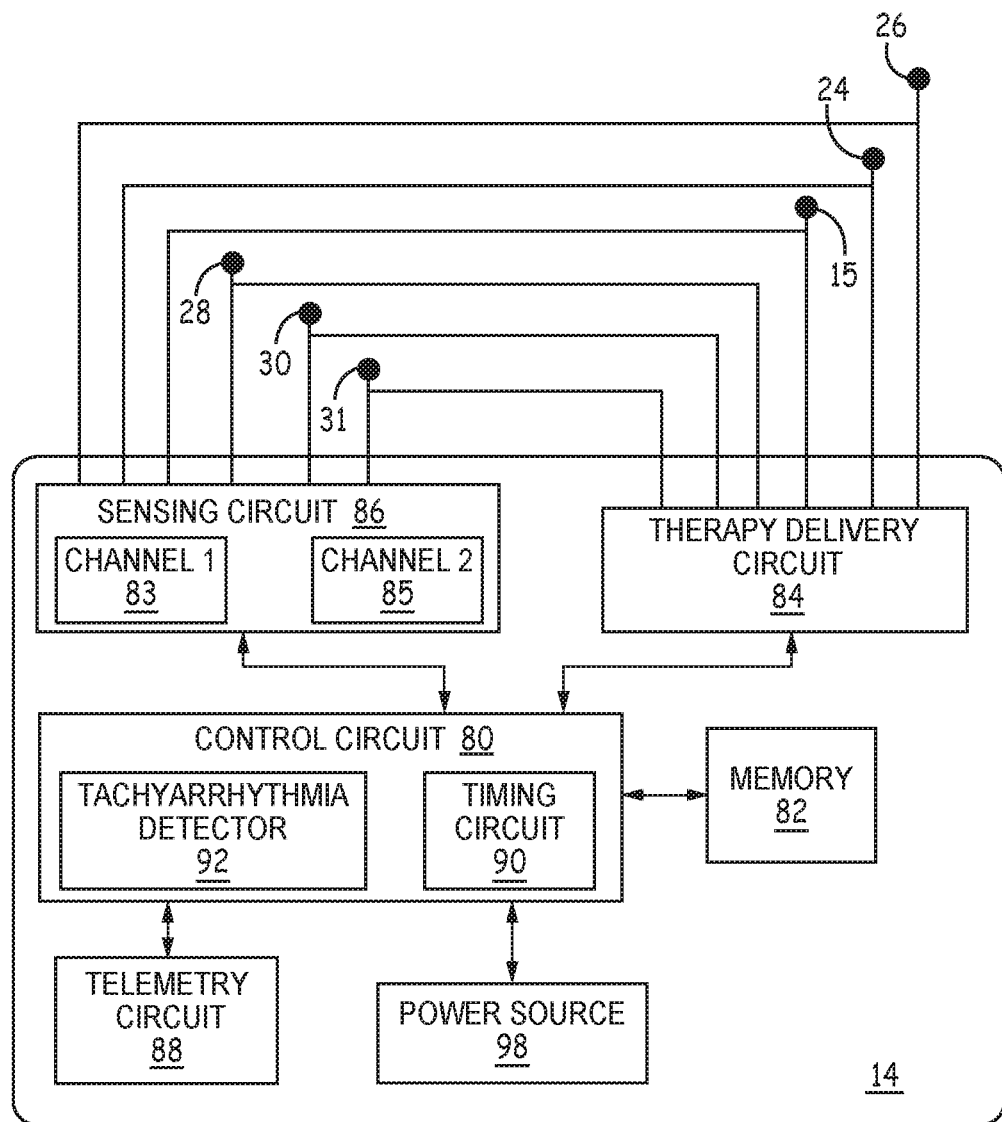
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT and VF for determining when ATP or CV/DF shocks are required. ICD 14 is coupled to an extra-cardiovascular lead, such as lead 16 carrying extra-cardiovascular electrodes 24, 26, 28, 30 and 31 (if present), for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering ATP, post-shock pacing or other pacing pulses instead of low voltage capacitors. Power source 98 is also coupled to components of sensing circuit 86, such as sense amplifiers, analog-to-digital converters, switching circuitry, etc. as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components. For example, cardiac event sensing and tachyarrhythmia detection operations may be performed by sensing circuit 86 under the control of control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 (if present as shown in FIGS. 1A and 2A) carried by lead 16 (e.g., as shown in FIGS. 1A-3) and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 is enabled to selectively receive cardiac electrical signals from at least two sensing electrode vectors from the available electrodes 24, 26, 28, 30, 31 and housing 15. At least two cardiac electrical signals from two different sensing electrode vectors may be received simultaneously by sensing circuit 86, and sensing circuit 86 may monitor one or both or the cardiac electrical signals at a time for sensing cardiac electrical signals. For example, sensing circuit 86 may include switching circuitry for selecting which of electrodes 24, 26, 28, 30, 31 and housing 15 are coupled to a sensing channel 83 or 85 including cardiac event detection circuitry, e.g., as described in conjunction with FIGS. 5 and 12. Switching circuitry may include a switch array, switch matrix, multiplexer, or any other type of switching device suitable to selectively couple components of sensing circuit 86 to selected electrodes. The cardiac event detection circuitry within sensing circuit 86 may include one or more sense amplifiers, filters, rectifiers, threshold detectors, comparators, analog-to-digital converters (ADCs), or other analog or digital components as described further in conjunction with FIGS. 5 and 12. A cardiac event sensing threshold may be automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86.

In some examples, sensing circuit 86 includes multiple sensing channels 83 and 85 for acquiring cardiac electrical signals from multiple sensing vectors selected from electrodes 24, 26, 28, 30, 31 and housing 15. Each sensing channel 83 and 85 may be configured to amplify, filter and digitize the cardiac electrical signal received from selected electrodes coupled to the respective sensing channel to improve the signal quality for detecting cardiac events, such as R-waves. For example, each sensing channel 83 and 85 may include a pre-filter and amplifier for filtering and amplifying a signal received from a selected pair of electrodes. The resulting raw cardiac electrical signal may be passed from the pre-filter and amplifier to cardiac event detection circuitry in at least one sensing channel 83 for sensing cardiac events from the received cardiac electrical signal in real time. As disclosed herein, sensing channel 83 may be configured to sense cardiac events such as R-waves based on a cardiac event sensing threshold, and second sensing channel 85 may be configured to pass a digitized cardiac electrical signal obtained from a different sensing electrode vector to control circuit 80 for use in confirming a cardiac event sensed by first sensing channel 83.

Upon detecting a cardiac event based on a sensing threshold crossing, first sensing channel 83 may produce a sensed event signal, such as an R-wave sensed event signal, that is passed to control circuit 80. The sensed event signal is used by control circuit 80 to trigger storage of a time segment of the second cardiac electrical signal for post-processing and analysis for confirming the R-wave sensed event signal as described below, e.g., in conjunction with FIGS. 7 through 9. Memory 82 may be configured to store a predetermined number of cardiac electrical signal segments in circulating buffers under the control of control circuit 80, e.g., at least one, two or other number of cardiac electrical signal segments. Each segment may be written to memory 82 over a time interval extending before and after the R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection.

The R-wave sensed event signals are also used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia episodes. Tachyarrhythmia detector 92 may be implemented in control circuit 80 as hardware and/or firmware that processes and analyzes signals received from sensing circuit 86 for detecting VT and/or VF. In some examples, the timing of R-wave sense event signals received from sensing circuit 86 is used by timing circuit 90 to determine RRIs between sensed event signals. Tachyarrhythmia detector 92 may include comparators and counters for counting RRIs determined by timing circuit 92 that fall into various rate detection zones for determining a ventricular rate or performing other rate- or interval-based assessment for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. When an interval counter reaches a detection threshold, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria. Examples of other parameters that may be determined from cardiac electrical signals received by sensing circuit 86 for determining the status of tachyarrhythmia detection rejection rules that may cause withholding to a VT or VF detection are described in conjunction with FIGS. 10, 11 and 13.

To support these additional analyses, sensing circuit 86 may pass a digitized electrocardiogram (ECG) signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82. Memory 82 may include one or more circulating buffers to temporarily store digital cardiac electrical signal segments for analysis performed by control circuit 80 to confirm R-waves sensed by sensing channel 83, determine morphology matching scores, detect T-wave oversensing, detect noise contamination, and more as further described below.

Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. Examples of devices and algorithms that may be adapted to utilize techniques for R-wave sensing and confirmation and tachyarrhythmia detection described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry; one or more charge storage devices, such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Timing circuit 90 of control circuit 80 may include various timers or counters that control when ATP or other cardiac pacing pulses are delivered. For example, timing circuit 90 may include programmable digital counters set by a microprocessor of the control circuit 80 for controlling the basic time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within timing circuit 90 are reset upon sensing of R-waves as indicated by signals from sensing circuit 86. In accordance with the selected mode of pacing, pacing pulses are generated by a pulse output circuit of therapy delivery circuit 84 when an escape interval counter expires. The pace output circuit is coupled to the desired pacing electrodes via a switch matrix for discharging one or more capacitors across the pacing load. The escape interval counters are reset upon generation of pacing pulses, and thereby control the basic timing of cardiac pacing functions, including ATP. The durations of the escape intervals are determined by control circuit 80 via a data/address bus. The value of the count present in the escape interval counters when reset by sensed R-waves can be used to measure RRIs by timing circuit 90 as described above for detecting the occurrence of a variety of arrhythmias by tachyarrhythmia detector 92.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured RRIs, counts or other data for analysis by the tachyarrhythmia detector 92 for predicting or diagnosing an arrhythmia.

In response to the detection of ventricular tachycardia, ATP therapy can be delivered by loading a regimen from the microprocessor included in control circuit 80 into timing circuit 90 according to the type and rate of tachycardia detected. In the event that higher voltage cardioversion or defibrillation pulses are required, e.g., the tachyarrhythmia is VF or the VT is not terminated via the ATP therapy, the control circuit 80 activates cardioversion and defibrillation control circuitry included in control circuit 80 to initiate charging of the high voltage capacitors via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by control circuit 80, a logic signal is generated on a capacitor full line passed to therapy delivery circuit 84, terminating charging. The defibrillation or cardioversion pulse is delivered to the heart under the control of the timing circuit 90 by an output circuit of therapy delivery circuit 84 via a control bus. The output circuit determines the electrodes used for delivering the cardioversion or defibrillation pulse and the pulse wave shape. Therapy delivery and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
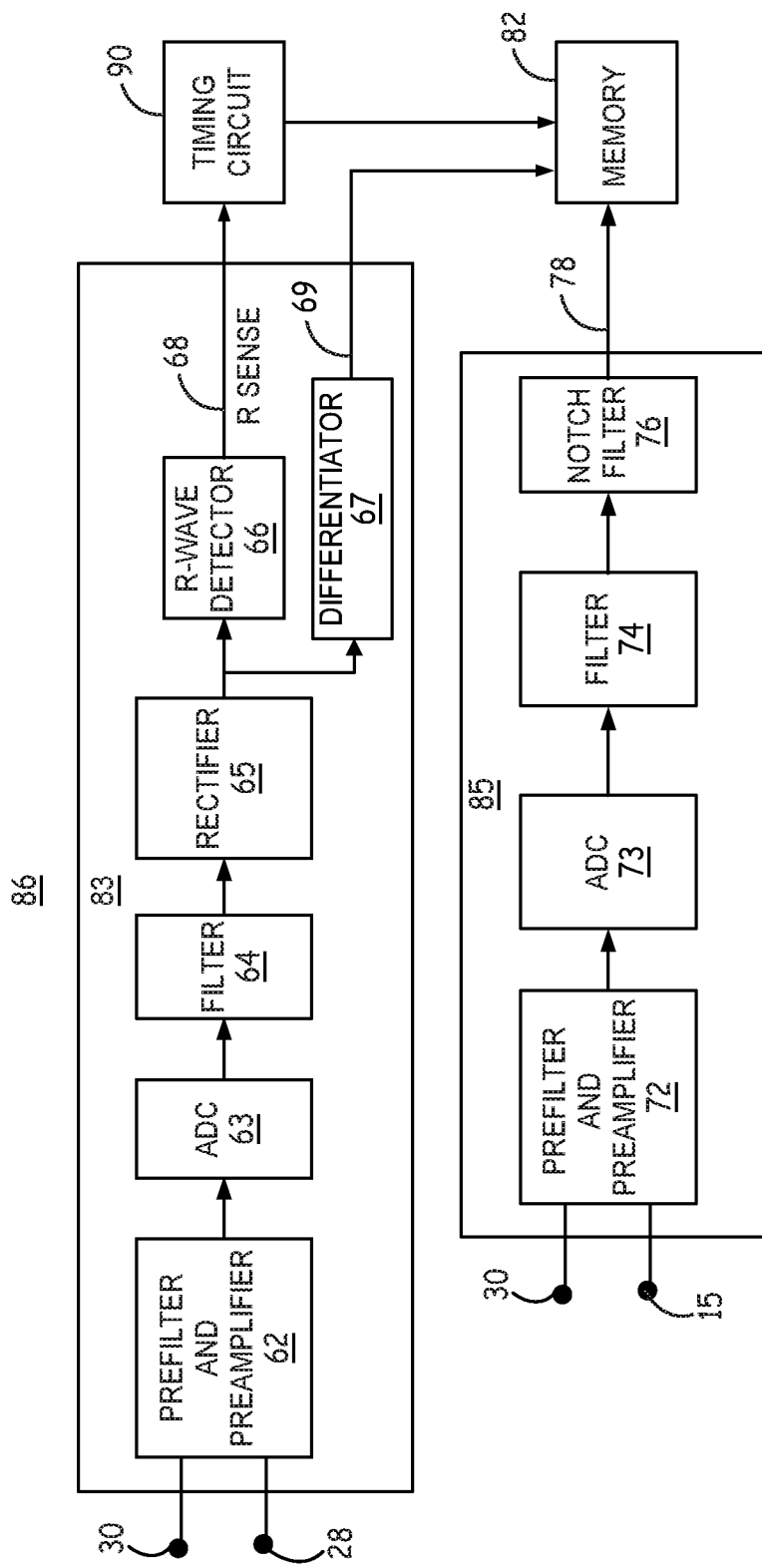
FIG. 5 is diagram of circuitry included in the sensing circuit of FIG. 4 according to one example.

FIG. 5 is diagram of circuitry included in first sensing channel 83 and second sensing channel 85 of sensing circuit 86 according to one example. First sensing channel 83 may be selectively coupled via switching circuitry (not shown) to a first sensing electrode vector including electrodes carried by extra-cardiovascular lead 16 as shown in FIGS. 1A-2C for receiving a first cardiac electrical signal. First sensing channel 83 may be coupled to a sensing electrode vector that is a short bipole, having a relatively shorter inter-electrode distance or spacing than the second electrode vector coupled to second sensing channel 85. In the example shown, the first sensing electrode vector may include pace/sense electrodes 28 and 30. In other examples, the first sensing electrode vector coupled to sensing channel 83 may include pace/sense electrodes 30 and 31 and in some cases pace/sense electrodes 28 and 31 depending on the inter-electrode spacing and position of the distal portion 25 of lead 16. In other examples, the first sensing channel 83 may be selectively coupled to a sensing electrode vector including a defibrillation electrode 24 and/or 26, e.g., a sensing electrode vector between pace/sense electrode 28 and defibrillation electrode 24, between pace/sense electrode 30 and either of defibrillation electrodes 24 or 26, or between pace/sense electrode 26 and 31, for example. In some examples, the first sensing electrode vector may be between defibrillation electrodes 24 and 26.

Sensing circuit 86 includes a second sensing channel 85 that receives a second cardiac electrical signal from a second sensing vector, for example from a vector that includes electrode 30 and housing 15, as shown, or a vector that includes electrode 28 and housing 15. Second sensing channel 85 may be selectively coupled to other sensing electrode vectors, which may form a long bipole having an inter-electrode distance or spacing that is greater than the sensing electrode vector coupled to first sensing channel 83. As described below, the second cardiac electrical signal received by second sensing channel 85 via a long bipole may be used by control circuit 80 for morphology analysis (including beat morphology analysis, noise rejection and other analyses, for example as described in conjunction with FIG. 10). In other examples, any vector selected from the available electrodes, e.g., electrodes 24, 26, 28, 30 and/or 31 and/or housing 15 may be included in a sensing electrode vector coupled to second sensing channel 85.

The electrical signals developed across input electrodes 28 and 30 of sensing channel 83 and across input electrodes 30 and 15 of sensing channel 85 are provided as differential input signals to the pre-filter and pre-amplifiers 62 and 72, respectively. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

In sensing channel 83, the digital output of ADC 63 is passed to filter 64 which may be a digital bandpass filter have a bandpass of approximately 10 Hz to 30 Hz for passing cardiac electrical signals such as R-waves typically occurring in this frequency range. The bandpass filtered signal is passed from filter 64 to rectifier 65 then to R-wave detector 66. R-wave detector 66 may include an auto-adjusting sense amplifier, comparator and/or other detection circuitry that compares the filtered and rectified first cardiac electrical signal to an R-wave sensing threshold in real time and produces an R-wave sensed event signal 68 when the cardiac electrical signal crosses the R-wave sensing threshold.

The R-wave sensing threshold may be controlled by sensing circuit 86 and/or control circuit 80 to be a multi-level sensing threshold as disclosed in U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval equal to a tachycardia detection interval, then drops to a second sensing threshold value held until a drop time interval expires, which may be 1 to 2 seconds long. The sensing threshold drops to a minimum sensing threshold after the drop time interval. The starting sensing threshold value may be the lower of a predetermined percentage of the most recent, preceding sensed R-wave peak amplitude and a maximum sensing threshold limit determined using a sensitivity-dependent gain and the programmed sensitivity setting. In other examples, the R-wave sensing threshold used by R-wave detector 66 may be set to a starting value based on a preceding R-wave peak amplitude and decay linearly or exponentially over time until reaching a minimum sensing threshold. However, the techniques of this application are not limited to a specific behavior of the sensing threshold. Instead, other automatically adjusted sensing thresholds may be utilized.

In some examples, the filtered, digitized cardiac electrical signal from sensing channel 83 (output of filter 64) may be stored in memory 82 for signal processing by control circuit 80 for use in detecting tachyarrhythmia episodes. In one example, the output of rectifier 64 is passed to differentiator 67 which determines an Nth order differential signal 69 that is passed to memory 82. The differential signal 69 is also sometimes referred to as a "difference signal" because each sample point of the differential signal 69 may be determined as the difference between the ith input sample point and a corresponding i-N input sample point. Control circuit 80 may retrieve the stored signal from memory 82 for performing signal analysis by tachyarrhythmia detector 92 according to implemented tachyarrhythmia detection algorithms. For example, a T-wave oversensing algorithm implemented in tachyarrhythmia detector 92 may detect evidence of T-wave oversensing from a first order differential signal 69 produced by differentiator 67 as described in U.S. Pat. Application No. 62/367,221, incorporated herein by reference in its entirety. Other examples of methods for detecting T-wave oversensing using a differential signal may be performed by tachyarrhythmia detector 92 as generally disclosed in U.S. Pat. No. 7,831,304 (Cao, et al.), incorporated herein by reference in its entirety.

The second cardiac electrical signal, digitized by ADC 73, may be passed to filter 74 for bandpass filtering, e.g., from 10 Hz to 30 Hz. In some examples, sensing channel 85 includes notch filter 76. Notch filter 76 may be implemented in firmware or hardware and is provided to attenuate 50-60 Hz electrical noise, muscle noise and other electromagnetic interference (EMI) or electrical noise/artifacts in the second cardiac electrical signal. Cardiac electrical signals acquired using extra-cardiovascular electrodes as shown, for example in FIGS. 1A-3, may be more likely to be contaminated by 50-60 Hz electrical noise, muscle noise and other EMI, electrical noise/artifacts than intra-cardiac electrodes. As such, notch filter 76 may be provided to significantly attenuate the magnitude of signals in the range of 50-60 Hz with minimum attenuation of signals in the range of approximately 1-30 Hz, corresponding to typical cardiac electrical signal frequencies. One example of a notch filter, designed with minimal computational requirements, and its filtering characteristics are described in conjunction with FIG. 6.

The output signal 78 of notch filter 76 may be passed from sensing circuit 86 to memory 82 under the control of control circuit 80 for storing segments of the second cardiac electrical signal 78 in temporary buffers of memory 82. For example, timing circuit 90 of control circuit 80 may set a time interval or number of sample points relative to an R-wave sensed event signal 68 received from first sensing channel 83, over which the second cardiac electrical signal 78 is stored in memory 82. The buffered, second cardiac electrical signal segment is analyzed by control circuit 80 on a triggered, as needed basis, as described in conjunction with FIGS. 7-13 to confirm R-waves sensed by the first sensing channel 83.

Notch filter 76 may be implemented as a digital filter for real-time filtering performed by firmware as part of sensing channel 85 or by control circuit 80 for filtering the buffered digital output of filter 74. In some examples, the output of filter 74 of sensing channel 85 may be stored in memory 82 in time segments defined relative to an R-wave sense event signal 68 prior to filtering by notch filter 76. When control circuit 80 is triggered to analyze the stored, second cardiac electrical signal for confirming an R-wave sensed event signal, for example as described in conjunction with FIGS. 7, 10, 11 and 13, the notch filter 76 may be applied to the stored segment of the second cardiac electrical signal before further processing and analysis of the stored segment. In this way, if analysis of the stored signal segment is not required for confirming an R-wave sensed by first sensing channel 83, firmware implemented to perform the operation of notch filter 76 need not be executed.

The configuration of sensing channels 83 and 85 is illustrative in nature and should not be considered limiting of the techniques described herein. The sensing channels 83 and 85 of sensing circuit 86 may include more or fewer components than illustrated and described in FIG. 5. First sensing channel 83, however, is configured to detect R-waves in real time, e.g., in hardware implemented components, from a first cardiac electrical signal based on crossings of an R-wave sensing threshold by the first cardiac electrical signal, and second sensing channel 85 is configured to provide a second cardiac electrical signal for storage in memory 82 for post-processing and analysis by control circuit 80 for confirming R-wave sensed event signals produced by the first sensing channel 83.

Figure 6:
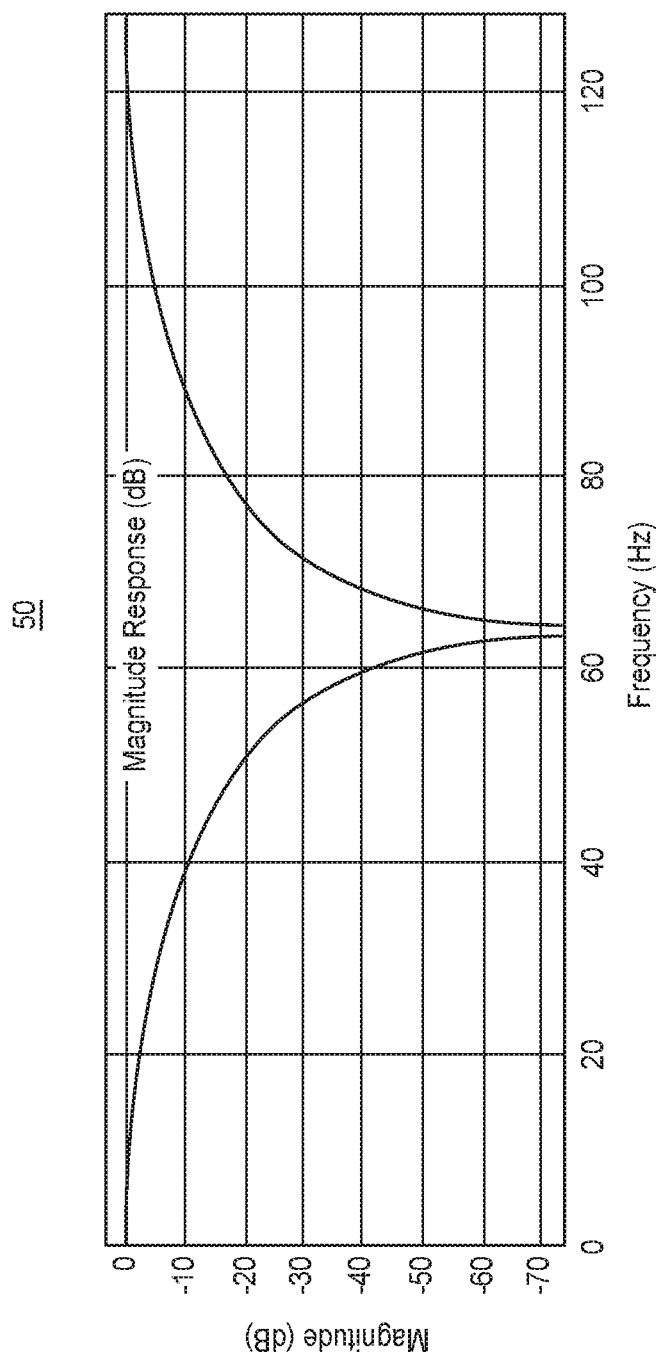
FIG. 6 is a plot of the attenuation characteristics of a notch filter that may be included in the sensing circuit of FIG. 5.

FIG. 6 is a plot 50 of the attenuation characteristics of notch filter 76 of the second sensing channel 85. In one example, notch filter 76 is implemented in firmware as a digital filter. The output of the digital notch filter may be determined by firmware implemented in the second sensing channel 85 according to the equation:

$$Y(n)=(x(n)+2x(n-2)+x(n-4))/4$$

where x(n) is the amplitude of the nth sample point of the digital signal received by the notch filter 76, x(n−2) is the amplitude of the n−2 sample point, and x(n−4) is the amplitude of the n−4 sample point for a sampling rate of 256 Hz. Y(n) is the amplitude of the nth sample point of the notch-filtered, digital second cardiac electrical signal. The plot 50 of FIG. 6 represents the resulting attenuation of the amplitude Y(n) as a function of frequency. At a frequency of 60 Hz, the attenuation of the magnitude of Y(n) is −40 decibels (dB). At a frequency of 50 Hz, the attenuation is −20 dB, and at 23 Hz, which may be typical of an R-wave of the cardiac electrical signal, the attenuation is limited to −3 dB. Notch filter 76 may therefore provide highly attenuated 50 and 60 Hz noise, muscle noise, other EMI, and other electrical noise/artifacts while passing lower frequency cardiac signals in the second cardiac electrical signal output of sensing channel 85. Although the notch filter 76 may not attenuate frequencies approaching the maximum frequency of 128 Hz, filter 74 of second sensing channel 85, which may be a bandpass filter, may adequately reduce the higher frequency range signal content above 60 Hz.

The sample point numbers indicated in the equation above for determining a notch-filtered signal may be modified as needed when a different sampling rate other than 256 Hz is used, however, the resulting frequency response may or may not be the same as that shown in FIG. 6. The notch filter 76 uses minimal computations with only two adds and three shifts required. In other examples, other digital filters may be used for attenuation of 50 and 60 Hz. For example, a sampling rate of 256 Hz, a filtered signal Y(n) may be determined as Y(n)=(x(n)+x(n−1)+x(n−2)+x(n−3))/4 which has less attenuation at 50 and 60 Hz than the frequency response shown in FIG. 6 but acts as a low-pass, notch filter with greater attenuation at higher frequencies (greater than 60 Hz) than the frequency response shown FIG. 6.

Figure 7:
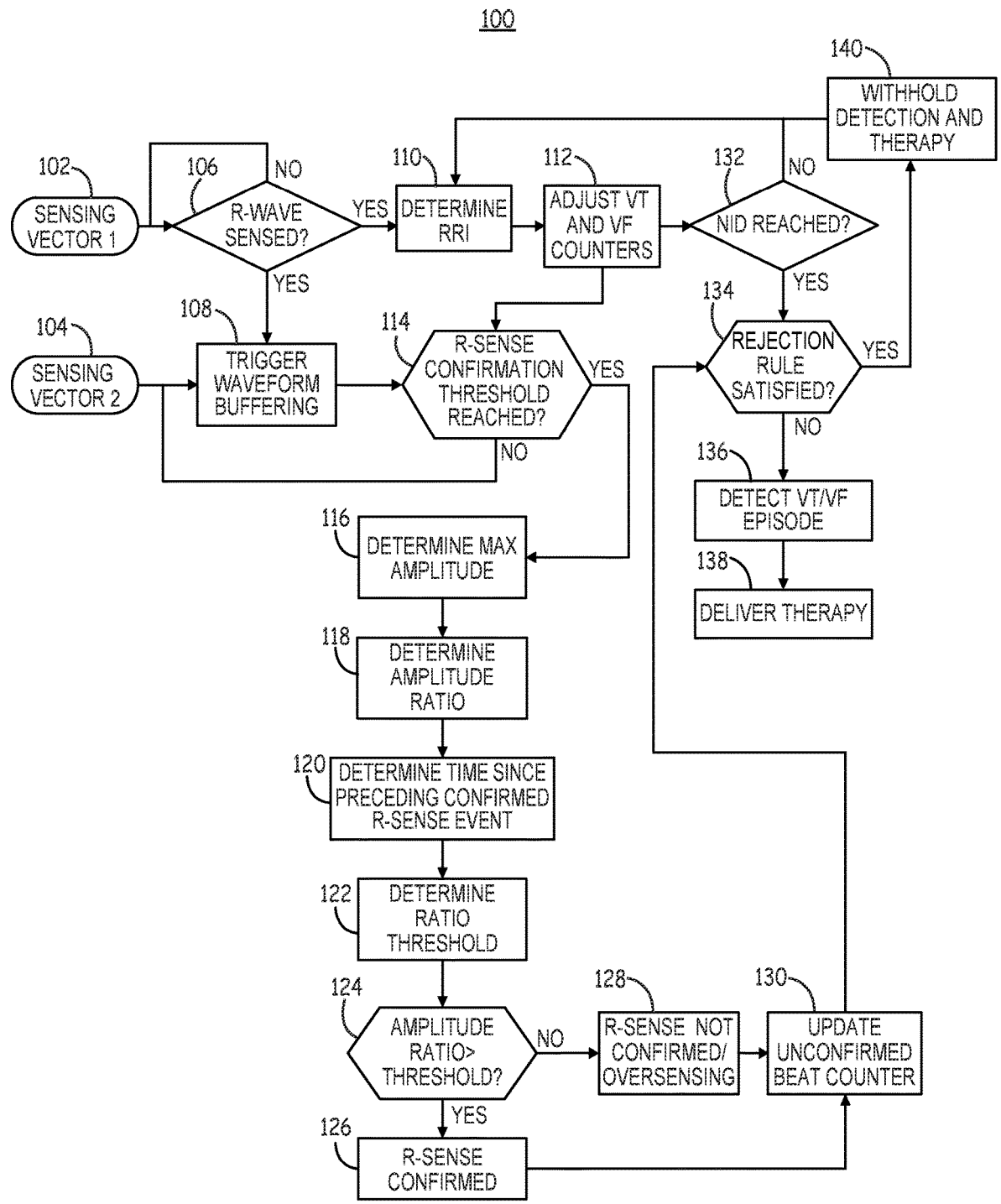
FIG. 7 is a flow chart of a method performed by the ICD of FIGS. 1A-2C for sensing and confirming R-waves for use in tachyarrhythmia detection according to one example.

FIG. 7 is a flow chart 100 of a method performed by ICD 14 for sensing and confirming R-waves for use in tachyarrhythmia detection according to one example. At blocks 102 and 104, two different sensing electrode vectors are selected by sensing circuit 86 for receiving a first cardiac electrical signal by a first sensing channel 83 and a second cardiac electrical signal by a second sensing channel 85. The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

The first sensing vector selected at block 102 for obtaining a first cardiac electrical signal may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers compared to other available sensing electrode pairs. The first sensing vector may be a vertical sensing vector (with respect to an upright or standing position of the patient) or approximately aligned with the cardiac axis for maximizing the amplitude of R-waves in the first cardiac electrical signal for reliable R-wave sensing.

The second sensing electrode vector used to obtain a second cardiac electrical signal at block 104 may be a relatively long bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This sensing vector may be orthogonal or almost orthogonal to the first sensing vector in some examples, but the first and second sensing vectors are not required to be orthogonal vectors. The second sensing electrode vector may provide a relatively more global or far-field cardiac electrical signal compared to the first sensing electrode vector. The second cardiac electrical signal obtained at block 104 may be used for waveform morphology analysis by the tachyarrhythmia detector 92 of control circuit 80 and is used for cardiac signal analysis for confirming an R-wave sensed event signal produced by first sensing channel 83 of sensing circuit 86.

Sensing circuit 86 may produce an R-wave sensed event signal at block 106 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 106, control circuit 80 is triggered at block 108 to store a segment of the second cardiac electrical signal received from the second sensing channel 85 (sensing vector 2, block 104) in a circulating buffer of memory 82. A digitized segment of the second cardiac electrical signal may be 100 to 500 ms long, for example, including sample points before and after the time of the R-wave sensed event signal, which may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the cardiac electrical signal is at least 50 sample points obtained at a sampling rate of 256 Hz, or about 200 ms. In another example, the buffered segment is at least 92 sample points, or approximately 360 ms, sampled at 256 Hz and is available for morphology analysis, noise analysis, T-wave oversensing, and/or other analysis performed by tachyarrhythmia detector 92 for detecting VT or VF. Other analyses of the buffered second cardiac electrical signal that may be performed by tachyarrhythmia detector 92 for detecting VT or VF, or withholding detection of VT or VF, are described in conjunction with FIG. 10. Memory 82 may be configured to store a predetermined number of second cardiac electrical segments, e.g., at least 1 and in some cases two or more cardiac electrical signal segments, in circulating buffers such that the oldest segment is overwritten by the newest segment. However, previously stored segments may never be analyzed for R-wave confirmation before being overwritten if an R-wave confirmation threshold is not reached as described below. In some examples, a single segment of the second cardiac electrical signal may be stored and if not needed for confirming an R-wave sensed by the first channel, the segment is overwritten by the next segment corresponding to the next R-wave sensed event signal.

In addition to buffering a segment of the second cardiac electrical signal, control circuit 80 responds to the R-wave sensed event signal produced at block 106 by determining an RRI at block 110 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 112. If the RRI is longer than a tachycardia detection interval (TDI), the tachyarrhythmia interval counters remain unchanged. If the RRI is shorter than the TDI but longer than a fibrillation detection interval (FDI), i.e., if the RRI is in a tachycardia detection interval zone, a VT interval counter is increased at block 112. If the RRI is shorter than or equal to the FDI, a VF interval counter is increased at block 112. In some examples, a combined VT/VF interval counter is increased if the RRI is less than the TDI.

After updating the tachyarrhythmia interval counters at block 112, tachyarrhythmia detector 92 compares the counter values to an R-sense confirmation threshold at block 114 and to VT and VF detection thresholds at block 132. If a VT or VF detection interval counter has reached an R-sense confirmation threshold, "yes" branch of block 114, the second cardiac electrical signal from sensing channel 85 is analyzed to confirm the R-wave sensed at block 106 by the first sensing channel 83. The R-sense confirmation threshold may be a VT or VF interval count that is greater than or equal to a count of one or another higher count value. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of intervals required to detect VT or VF. In addition or alternatively to applying an R-sense confirmation threshold to the individual VT and VF counters, an R-sense confirmation threshold may be applied to a combined VT/VF interval counter.

If the R-sense confirmation threshold is not reached by any of the tachyarrhythmia interval counters at block 114, the control circuit 80 waits for the next R-wave sensed event signal at block 108 to buffer the next segment of the second cardiac electrical signal. If the R-sense confirmation threshold is reached at block 114, the control circuit 80 determines a maximum amplitude at block 116 of the buffered signal segment stored for the most recent R-wave sensed event signal. The maximum amplitude may be determined from a differential signal determined from the buffered signal segment. For example, an nth-order differential signal may be determined from the buffered signal segment by determining a difference between the ith and the ith-n signal sample points of the buffered signal segment. In one example a 4th order differential signal is determined.

The maximum absolute value of the differential signal is estimated as the amplitude of the event in the second cardiac electrical signal that was sensed as an R-wave from the first cardiac electrical signal. The time of the maximum absolute value of the signal is identified as the time of the event in the second cardiac electrical signal. When the R-wave is not the first R-wave to be confirmed since the R-sense confirmation threshold was reached, the control circuit 80 determines an amplitude ratio at block 118 as the ratio of the maximum absolute value determined at block 116 to the event amplitude determined from the second cardiac electrical signal for the most recently confirmed R-wave sensed event. At block 120, the control circuit 80 determines a time interval from the most recent event of the second cardiac electrical signal confirmed as an R-wave sensed event to the time of the event determined at block 116.

When the R-wave is the first R-wave to be confirmed after the R-sense confirmation threshold is reached, the first confirmed event on the second cardiac electrical signal may be assumed to occur at the same time as the R-wave sensed event signal with a default maximum amplitude. The default maximum amplitude may be set equal to the amplitude of the R-wave sensed by the first sensing channel 83, a nominal value, e.g., 1 millivolt, or a previously determined R-wave amplitude or average R-wave amplitude determined from the second cardiac electrical signal. Alternatively, the maximum absolute amplitude of the differential signal and its time may be identified and stored as initial values used for determining an amplitude ratio and time at blocks 118 and 120 for the next R-wave to be confirmed. In other examples, an amplitude ratio may be determined for the first R-wave to be confirmed after the R-sense confirmation threshold is reached using a previously determined R-wave amplitude, e.g., from a prior time that the R-sense confirmation threshold was reached or a default R-wave amplitude. The first R-wave may be confirmed based on this amplitude ratio and/or time since the preceding R-wave sensed event signal.

At block 122, the control circuit 80 determines a ratio threshold to be applied to the amplitude ratio based on the time interval determined at block 120. In one example, the ratio threshold is retrieved from a look-up table stored in memory. In other examples, the ratio threshold may be computed as a function of the time interval determined at block 120. The ratio threshold may be a variable threshold that decreases as the time interval since the most recent confirmed R-wave increases. As such, the time interval determined at block 120 is used to determine what ratio threshold should be applied to the amplitude ratio determined at block 118 for confirming the R-wave sensed by first sensing channel 83. The ratio threshold may decrease in a linear, exponential or stepwise manner, or a combination thereof. For instance, the ratio threshold may decrease with a continuous slope or decay rate over some portions of time since the most recent confirmed R-wave and may be held constant over other portions of time since the most recent confirmed R-wave. An example of a time-varying ratio threshold and method for determining the ratio threshold at block 122 is described in conjunction with FIGS. 8 and 9.

At block 124, control circuit 80 compares the ratio threshold determined at block 122 to the amplitude ratio determined at block 118. If the amplitude ratio is equal to or greater than the ratio threshold, the R-wave sensed event is confirmed at block 126. If the amplitude ratio is less than the ratio threshold, the R-wave sensed event is not confirmed at block 128. The event may be an oversensed T-wave, P-wave, muscle noise, electromagnetic interference or other or non-cardiac electrical noise that has been oversensed by the first sensing channel 83.

At block 130 the control circuit 80 adjusts an unconfirmed beat counter. If the R-wave sensed event is not confirmed, the unconfirmed beat counter is increased by one count. If the R-wave sensed event is confirmed at block 126, the unconfirmed beat counter may be kept at its current value or decreased. In some examples, the unconfirmed beat counter tracks how many out of the most recent predetermined number of consecutive R-wave sensed event signals produced by first sensing channel 83 are not confirmed in an x out of y manner. For example, the unconfirmed beat counter may track how many out of the most recent 12 R-wave sensed event signals are not confirmed to be R-waves based on the amplitude ratio comparison made at block 124.

In addition to counting how many beats are unconfirmed at block 130, data relating to the most recent n events analyzed by control circuit 80 may be stored in a rolling buffer. For example, data may be stored for the most recent twelve events analyzed for confirming an R-wave sensed event signal. The stored data may include the event amplitude, the amplitude ratio, the event timing, the time interval since the most recent confirmed event, and whether the event was confirmed or not confirmed.

While the R-wave sensed event signal is either confirmed or not confirmed based on an amplitude ratio determined from the second cardiac electrical signal according to the example of FIG. 7, it is recognized that other features of the second cardiac signal may be compared to R-wave confirmation criteria in addition to or instead of the event amplitude as described above. For example, a peak slew rate, an event area, an event signal width, or other features of the buffered cardiac electrical signal segment may be compared to respective thresholds for confirming the event as being an R-wave. The thresholds may be defined as a minimum ratio of the feature relative to an analogous feature of the most recent preceding event confirmed to be an R-wave or may be thresholds compared directly to features determined from the buffered cardiac electrical signal segment independent of preceding events.

If any of the tachyarrhythmia interval counters adjusted at block 112 reach a number of intervals to detect (NID) tachyarrhythmia, as determined at block 132, tachyarrhythmia detector 92 of control circuit 80 determines whether a rejection rule is satisfied at block 134 before detecting the tachyarrhythmia. In one example, the NID required to detect VT may be a count of 16 VT intervals, which are RRIs that fall into a predetermined VT interval range or zone. The NID to detect VF may be a count of 30 VF intervals out of the last 40 RRIs where the VF intervals are RRIs that fall into a predetermined VF interval range or zone. If an NID is reached, one or more rejection rules may be applied for rejecting a VT or VF detection based on RRI counts satisfying the NID. Various rejection rules are described below, e.g., in conjunction with FIGS. 10, 11 and 13. At least one rejection rule may relate to the number of R-waves sensed by the first sensing channel 83 that were not confirmed by the analysis of the second cardiac electrical signal. Another rejection rule may relate to the detection of noisy signal segments based on gross morphology analysis as described in conjunction with FIGS. 14 through 19.

For instance, the unconfirmed beat counter updated at block 130 may be compared to a rejection rule criterion at block 134. The rejection rule criterion may be a rejection threshold requiring that at least x of y events are not confirmed R-waves. For example, if at least 3, at least 4, at least 6 or other predetermined number of the most recent 12 events (or other predetermined number of events) analyzed for confirming an R-wave sensed event signal are not confirmed R-waves, the rejection rule is satisfied, "yes" branch of block 134. The pending VT or VF detection based on the NID being reached at block 132 is withheld at block 140, and no anti-tachyarrhythmia therapy is delivered.

If all rejection rules are not satisfied, "no" branch of block 134, the pending detection of the VT or VF episode is not withheld. VT or VF is detected at block 136 based on the respective VT or VF interval counter reaching a corresponding NID. Control circuit 80 controls therapy delivery circuit 84 to deliver an appropriate anti-tachyarrhythmia therapy, e.g., ATP or a cardioversion/defibrillation shock, according to programmed therapy control parameters.

Figures 8, 9:
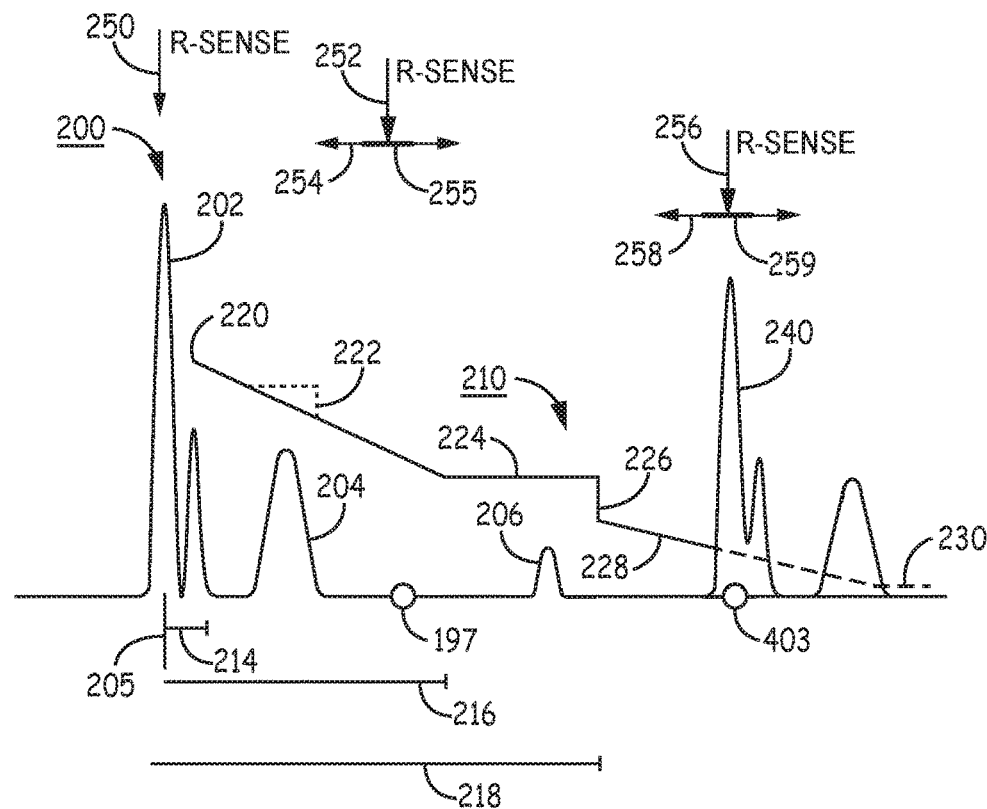
FIG. 8 is a diagram of a filtered cardiac electrical signal and an amplitude ratio threshold that may be applied for confirming R-wave sensed events.
FIG. 9 is an example of a look-up table of amplitude ratio threshold values that may be stored in memory of the ICD of FIGS. 1A-2C for use in confirming R-wave sensed events.

FIG. 8 is a diagram of a filtered, second cardiac electrical signal 200 and an amplitude ratio threshold 210 that may be applied to the amplitude ratio determined from the second cardiac electrical signal at block 118 of FIG. 7 for confirming an R-wave sensed event signal from the first sensing channel 83. The amplitude ratio is not a sensing threshold that is compared to the second cardiac electrical signal 200 in real time. The first sensing channel 83 may operate by sensing an R-wave when the first cardiac electrical signal crosses an R-wave amplitude sensing threshold defined in mV. The second cardiac electrical signal provided to control circuit 80 by the second sensing channel 85, however, is not compared to an amplitude sensing threshold in real time as it is acquired. Rather, as described in conjunction with FIG. 7, if the first sensing channel 83 produces an R-wave sensed event signal, the second cardiac electrical signal is buffered in memory 82 and if a tachyarrhythmia interval counter reaches an R-wave confirmation threshold, the buffered signal is post-processed to determine if the ratio of a maximum amplitude determined from the buffered signal segment to the maximum amplitude determined from a preceding confirmed R-wave of the second cardiac electrical signal reaches or exceeds the ratio threshold 210.

The ratio threshold 210 is shown relative to the second cardiac electrical signal 200 because the ratio threshold 210 is not a fixed value but varies over time. Ratio threshold 210 decreases as the time since the confirmed R-wave 202 increases. This time-variant ratio threshold is why the control circuit 80 determines the time since the preceding confirmed R-wave sensed event at block 120 of FIG. 7 in order to determine the value of the ratio threshold at block 122 that is applied to the amplitude ratio for confirming or not confirming the R-wave sensed event signal.

Cardiac electrical signal 200 may be produced by the second sensing channel 85 by filtering, amplifying and digitizing the cardiac electrical signal received by the second sensing electrode vector. While signal 200 is shown conceptually as having only positive-going waveforms it is to be understood that signal 200 may have positive- and negative-going portions and need not be a rectified signal. The absolute value of the maximum peak amplitude, positive or negative, may be determined from the stored second cardiac electrical signal segment at block 116 of FIG. 7. Cardiac electrical signal 200 includes an R-wave 202, a T-wave 204, a P-wave 206, and a subsequent R-wave 240. R-wave 202 represents a confirmed event occurring at time point 205. Time point 205 is the sample point of the maximum absolute value of the differential signal determined in response to an R-wave sense event signal 250 as described above in conjunction with FIG. 7.

If an R-wave sensed event signal occurs during a blanking interval 214 following time point 205 of a preceding confirmed R-wave 202, the new R-wave sensed event is not confirmed. Sensing channel 83 may have sensed the same R-wave 202 twice or sensed non-cardiac electrical noise as an R-wave.

After the blanking interval, the ratio threshold 210, at a time point corresponding to the expiration of blanking interval 214, is equal to a starting value 220 which may be set to 0.6 in one example, but may range between 0.4 and 0.7 in other examples. In one implementation, the ratio threshold 210 is stored in a look-up table and retrieved from memory 82 by control circuit 80 for comparison to an amplitude ratio determined in response to an R-wave sensed event signal from the first sensing channel.

FIG. 9 is an example of a look-up table 300 of ratio threshold values 304 that may be stored in memory 82 for respective event time intervals, which may be stored as corresponding sample point numbers 302. If the blanking interval 214 is approximately 150 ms, the first sample point at which a maximum amplitude may be determined as an event time point is at sample point 38 when the sampling rate is 256 Hz. In other examples, blanking interval 214 may be longer or shorter than 150 ms and the first sample point number stored in look-up table 300 will correspond to the sample point number at which the blanking interval 214 expires after the confirmed event time point 205, considered to "zero" sample point.

The ratio threshold is stored for the first sample point number entry as being the starting ratio threshold value 220, which is 0.6 in this example. If the control circuit 80 receives an R-wave sensed event signal from the first sensing channel 83, and a detection interval counter is equal to or greater than the R-wave confirmation threshold, a maximum event amplitude and event time is determined from the buffered, second cardiac electrical signal. The event time may be determined as the sample point number since the event time 205 of the most recent confirmed R-wave 202. If the event time is determined to be sample point number 38, control circuit 80 retrieves the ratio threshold, 0.6 in this example, stored in the look-up table 300 for the sample point number 38. This ratio threshold value is applied to the amplitude ratio determined from the maximum amplitude of the buffered, second cardiac electrical signal to the maximum amplitude determined from the most recent confirmed R-wave 202.

Referring again to FIG. 8, the ratio threshold 210 is shown to decrease at a constant decay rate 222 until the expiration of a first time interval 216. Time interval 216 may be defined to start at the time point 205 of the confirmed event 202 or start upon expiration of blanking interval 205. Time interval 216 may extend for up to 1 second from the time point 205 of the most recent confirmed R-wave 202. The decay rate 222 may, in one example, be approximately 0.3/second so that if time interval 216 is approximately 1 second, ratio threshold value 224 is 0.3 when the starting ratio threshold value 220 is 0.6.

Beginning at the expiration of time interval 216, ratio threshold 210 is held at a constant value 224 until a second time interval 218 expires. The constant value 224 is a ratio of approximately ⅓ (0.3) in one example but may be between ⅕ (0.2) and ½ (0.5) in other examples. Value 224 may be held for up to 500 ms after time interval 216 expires (for a total time interval 218 of up to 1.5 seconds). This change from the decay rate 222 to the constant value 224 is reflected in look-up table 300 as the ratio threshold 0.3 starting at sample point number 256 extending through sample point number 383.

At the expiration of time interval 218, the ratio threshold 210 drops stepwise to an intermediate ratio threshold value 226 then decays at a constant rate 228 until it reaches a minimum ratio threshold 230. The step drop from constant value 224 may be a drop to a ratio threshold of approximately ⅙ to ¼. In one example, the ratio threshold drops from approximately ⅓ (0.3) to an intermediate ratio threshold of ⅕ (0.2) at 0.5 seconds after the expiration of time interval 216. This change is reflected in look-up table 300 as the ratio threshold of 0.2 at sample point 384 (0.5 seconds after sample point 256).

The second decay rate 228 may be the same as decay rate 222 or a slower decay rate such that ratio threshold 210 reaches the minimum ratio threshold 230, e.g., ⅟32 (0.03), ⅟64 (0.015) or other predetermined minimum ratio, approximately 2.5 seconds (sample point number 640) after the time point 205 of the preceding confirmed R-wave 202. The behavior of ratio threshold 210 moving forward in time from confirmed R-wave 202 is captured in look-up table 300 (FIG. 9). For example, at the example decay rate 222 of 0.3/second, the ratio threshold is 0.587 at sample point number 48, and so on.

The values recited here and reflected in look-up table 300 for ratio threshold values 220, 224, and 226 and 230 and time intervals 216 and 218 are illustrative in nature; other values less than or greater than the recited values may be used to implement a time-varying ratio amplitude for use in confirming an R-wave sensed event. The values for the ratio thresholds and time intervals used to control changes from one ratio threshold value to another or a decay rate and total decay interval will depend in part on the sampling rate, which is 256 Hz in the examples provided but may be greater than or less than 256 Hz in other examples.

Referring again to FIG. 8, if an R-wave sensed event signal 252 is produced by first sensing channel 83, control circuit 80 is triggered to store a time segment 254 of the second cardiac electrical signal 200 in memory 80. Time segment 254 may be 360 ms in one example, and may be between 300 ms and 500 ms in other examples. If a VT or VF or combined VT/VF interval counter has reached an R-wave confirmation threshold, control circuit 80 determines a maximum amplitude from the buffered cardiac signal time segment. As described above, the maximum amplitude may be the maximum absolute value of an x-order differential signal determined from the second cardiac electrical signal 200. The maximum amplitude may be determined from a portion of the stored cardiac signal time segment. For example, the maximum amplitude may be determined from a segment 255 that is a sub-segment or portion of the stored time segment 254. Segment 255 may be approximately 50 to 300 ms long, e.g., 200 ms long, when the total time segment 254 is 360 ms to 500 ms long. The segment 255 may be defined relative to the time the R-wave sensed event signal 252 is received.

The sample point number 197 at which the maximum amplitude within the time segment 255 occurs represents the number of sample points since the event time 205 (sample point number zero) of the most recent confirmed R-wave 202. The sample point number 197 is determined as the event time of the maximum amplitude of cardiac signal time segment 255. Control circuit 80 uses this sample point number to look up the corresponding ratio threshold 304 in look-up table 300. For the sake of example, the maximum amplitude during time segment 255 obtained in response to R-wave sensed event signal 252 may occur at sample point number 197 approximately 0.77 seconds after event time point 205. The stored ratio threshold for sample point number 197 may be approximately 0.4 for a decay rate 222 of approximately 0.3/second (or 0.0012 per sample point) from the starting value 220, which is 0.6 beginning at sample point number 38 in this example. If the amplitude ratio of the maximum amplitude determined at sample point number 197 during time segment 255 to the maximum amplitude determined for confirmed R-wave 202 is greater than or equal to 0.4, R-wave sensed event 252 is confirmed. In this example, the cardiac electrical signal has a low, baseline amplitude during interval 255, and as such the R-wave sensed event signal 252 is not confirmed. Control circuit 80 increases the unconfirmed event counter as described in conjunction with FIG. 7.

Similarly, control circuit 80 may receive R-wave sensed event signal 256 and determine a maximum amplitude during time segment 259, defined relative to R-wave sensed event signal 256, of the buffered cardiac electrical signal segment 258. The event time sample point number 403 at which the maximum amplitude occurs since event time 205 is used to look up the ratio threshold from look up table 300. In this case, the amplitude ratio determined from the buffered, second cardiac electrical signal during time segment 259 exceeds the ratio threshold 210 at the event time sample point number 403 of the maximum amplitude during time segment 259, which corresponds to R-wave 240. R-wave sensed event signal 256 is confirmed by control circuit 80. In this way, the second cardiac electrical signal from sensing channel 85 is analyzed only when an R-wave sensed event confirmation condition is met, e.g., a tachyarrhythmia interval counter is active and has reached a threshold count, which may be less than a required number of intervals to detect a VT or VF episode. The R-wave sensed event of the first sensing channel is confirmed based on post-processing of the buffered, second cardiac electrical signal.

Figure 10:
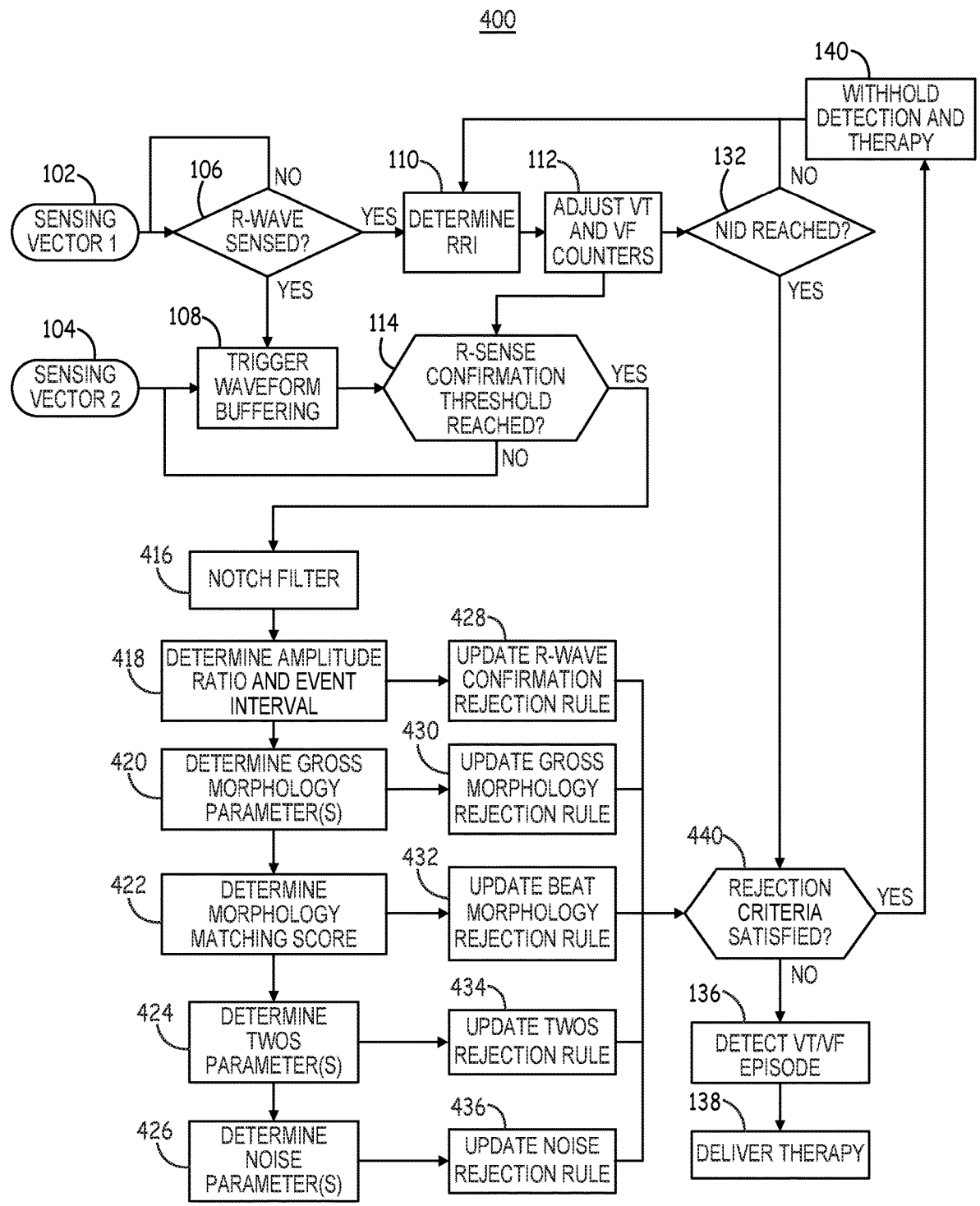
FIG. 10 is a flow chart of a method for detecting tachyarrhythmia by an ICD according to one example.

FIG. 10 is a flow chart 400 of a method for detecting tachyarrhythmia by ICD 14 according to another example. Operations performed at blocks 102-114, 132, 136, 138 and 140 in flow chart 400 may generally correspond to identically-numbered blocks shown in FIG. 7 and described above. At blocks 102 and 104, two different sensing electrode vectors are selected by sensing circuit 86 for receiving a first cardiac electrical signal by first sensing channel 83 and a second cardiac electrical signal by second sensing channel 85 as described above in conjunction with FIGS. 5 and 7.

Sensing circuit 86 may produce an R-wave sensed event signal at block 106 in response to the first sensing channel 83 detecting an R-wave sensing threshold crossing by the first cardiac electrical signal. The R-wave sensed event signal may be passed to control circuit 80. In response to the R-wave sensed event signal, control circuit 80 is triggered at block 108 to store a segment of the second cardiac electrical signal received from the second sensing channel 85 in a circulating buffer of memory 82. A digitized segment of the second cardiac electrical signal, which may be defined in time relative to the time of the R-wave sensed event signal received from sensing circuit 86, and may be 100 to 500 ms long, for example. In one example, the buffered segment of the cardiac electrical signal is at least 92 sample points obtained at a sampling rate of 256 Hz, or approximately 360 ms, of which 68 sample points may precede and include the sample point at which the R-wave sensed event signal was received and 24 sample points may extend after the sample point at which the R-wave sensed event signal was received.

In addition to buffering a segment of the second cardiac electrical signal, control circuit 80 responds to the R-wave sensed event signal produced at block 106 by determining an RRI at block 110 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia detection counters at block 112 as described above in conjunction with FIG. 7.

After updating the VT and VF interval counters at block 112, tachyarrhythmia detector 92 compares the interval counter values to an R-sense confirmation threshold at block 114 and to VT and VF NID detection thresholds at block 132. If a VT or VF interval counter has reached an R-sense confirmation threshold, "yes" branch of block 114, the second cardiac electrical signal from sensing channel 85 is analyzed to confirm the R-wave sensed at block 106 by the first sensing channel 83. The R-sense confirmation threshold is a count of two on the VT interval counter and a count of 3 on the VF interval counter in one example. Other examples are given above in conjunction with FIG. 7.

If the R-sense confirmation threshold is not reached by any of the interval counters at block 114, the control circuit 80 waits for the next R-wave sensed event signal at block 108 to buffer the next segment of the second cardiac electrical signal. In some cases, the oldest buffered cardiac signal segment may be overwritten by the next cardiac signal segment without ever being analyzed for confirming an R-wave, or analyzed for any other purpose, since analysis of the buffered cardiac signal segment is not required if the VT and VF interval counters are inactive (at a count of zero) or remain below the R-sense confirmation threshold.

If an R-sense confirmation threshold is reached at block 114, the control circuit 80 applies a notch filter to the stored, second cardiac electrical signal segment at block 416. The notch filter applied at block 416 may correspond to the filter described in conjunction with FIG. 6. The notch filter significantly attenuates 50-60 Hz electrical noise, muscle noise, other EMI, and other noise/artifacts in the stored, second cardiac electrical signal segment. Using the notch filtered segment, control circuit 80 performs multiple analyses on the segment to determine if any rejection rules are satisfied. As described below, if a rejection rule is satisfied, a pending VT or VF episode detection made based on an NID threshold being reached at block 132 may be withheld.

As described in conjunction with FIG. 7, an amplitude ratio may be determined at block 418 for confirming the R-wave sensed event signal that triggered the buffering of the currently stored, second cardiac electrical signal segment. Determinations made at block 418 may include the operations performed at blocks 116, 118 and 120 of FIG. 7. The amplitude ratio is used to update an R-wave confirmation rejection rule at block 428.

The maximum peak amplitude used to determine the amplitude ratio may be determined from a portion of the stored cardiac signal segment at block 418. For example, if a 360 ms or 500 ms segment is stored at block 108, only a 200 ms segment, e.g., approximately 52 sample points sampled at 256 Hz, which may be centered in time on the R-wave sensed event signal may be analyzed for determining the amplitude ratio at block 418. A longer signal segment may be stored at block 108 than required for determining the amplitude ratio at block 418 so that a longer segment is available for other signal analysis procedures performed by tachyarrhythmia detector 92 as described below, e.g., for determining a baseline noise parameter and other gross morphology parameters for detecting noisy signal segments as described in conjunction with FIGS. 14 through 19.

Control circuit 80 may determine an event interval at block 418 as the time interval or number of sample points from the maximum peak amplitude to the preceding confirmed R-wave sensed event, when the current R-wave sensed event signal is not the first one being confirmed since the R-sense confirmation threshold was reached at block 114. At block 428, control circuit 80 may compare the amplitude ratio to a ratio threshold, which may be retrieved from a look-up table stored in memory 82 using the determined event interval as described in conjunction with FIGS. 8 and 9. If the amplitude ratio is greater than the ratio threshold, the sensed R-wave is confirmed. If the amplitude ratio is less than the ratio threshold, the sensed R-wave is not confirmed.

An X of Y unconfirmed beat counter may be updated by tachyarrhythmia detector 92 at block 428 to reflect the number of R-wave sensed event signals that are not confirmed out of the most recent Y R-wave sensed event signals. For example, the X of Y counter may count how many R-waves are not confirmed to be R-waves out of the most recent 12 R-wave sensed event signals. If the X of Y count reaches a rejection threshold, e.g., if at least 3, 4, 5 or another predetermined number out of 12 R-wave sensed event signals are not confirmed to be R-waves, the R-wave rejection rule for withholding tachyarrhythmia detection is satisfied. A flag or logic value may set by control circuit 80 to indicate the R-wave rejection rule is satisfied. Updating the R-wave rejection rule at block 428 may include operations described in conjunction with FIG. 7 for blocks 122, 124, 126, 128, 130 and 134.

At blocks 420, 422, 424 and 426, other cardiac signal parameters may be determined from the notch-filtered, cardiac signal segment for updating the status of other tachyarrhythmia detection rejection rules at respective blocks 430, 432, 434 and 436. In some examples, a digitized cardiac electrical signal from first sensing channel 83 may be analyzed and used in updating the status of a tachyarrhythmia detection withhold rule. For example, the notch filtered, cardiac electrical signal from the second sensing channel 85 may be analyzed at blocks 420, 422 and 426 for updating a gross morphology rejection rule, a beat morphology rejection rule and a noise rejection rule at blocks 430, 432, and 436, respectively. The differential signal 69 (see FIG. 5) from the first sensing channel 83 may be analyzed at block 424 for updating the T-wave oversensing (TWOS) rule at block 434.

Figure 15:
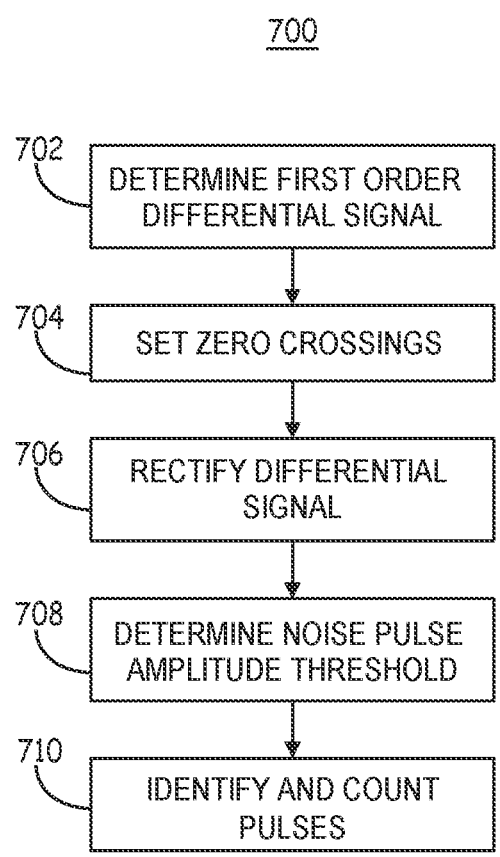
FIGS. 15, 16 and 17 are flow charts of illustrative methods for determining gross morphology parameters of a cardiac electrical signal that may be used in detecting a noisy signal segment.

At block 420 one or more gross morphology parameters are determined from the notch-filtered, second cardiac signal segment. Gross morphology parameters may include, but are not limited to, a low slope content, a noise pulse count, a normalized rectified amplitude, a maximum signal width, or other noise metrics. Examples of gross morphology parameters that may be determined at block 420 are described below in conjunction with FIGS. 15, 16 and 17. Other examples of gross morphology parameters that may be determined are generally disclosed in the above-incorporated U.S. Pat. No. 7,761,150 (Ghanem, et al.) and U.S. Pat. No. 8,437,842 (Zhang, et al.). The gross morphology parameters may be determined using the entire second cardiac signal segment stored at block 108 or a portion of the stored segment. In one example, at least 92 sample points, approximately 360 ms, are analyzed for determining the gross morphology parameters, which may be a portion of or the entire stored segment. The portion of the signal segment analyzed for determining gross morphology metrics extends beyond an expected QRS signal width so that at least a portion of the segment being analyzed corresponds to an expected baseline portion. In this way, at least one gross morphology parameter determined, such as the noise pulse count described in conjunction with FIG. 15, is correlated to non-cardiac signal noise that may be occurring during the baseline portion, such as non-cardiac myoelectric noise or electromagnetic interference (EMI).

The gross morphology parameters are used at block 430 to update the status of a gross morphology rejection rule. Gross morphology parameters are determined from the signal segment for determining whether the signal segment, and therefore the second cardiac electrical signal, is noisy. A noisy segment may include multiple noise signal pulses that are evidence of non-cardiac muscle (myoelectric) noise, EMI, or other non-cardiac noise signals. A noisy signal segment may be an indication that an R-wave sensed event signal during the noisy signal segment is not reliable for contributing to a VT or VF detection. The gross morphology analysis may therefore analyze signal segment sample points that are not limited to the R-wave but may extend along an expected baseline portion of the segment prior to the R-wave sensed event signal that triggers the storage of the signal segment. By performing signal morphology analysis that includes expected baseline portions, which may be referred to as "gross morphology analysis" since it involves analysis of an entire signal segment or an extended portion of the signal segment that extends beyond just an expected R-wave or QRS waveform, noise pulses may be identified and detected to enable detection of noisy signal segments.

Criteria or thresholds may be applied to each gross morphology parameter determined, and the gross morphology rejection rule may be satisfied when a required number of the gross morphology parameters meet the criteria or threshold applied to the respective parameter. For example, if at least two out of three gross morphology parameters satisfy noise detection criteria, the gross morphology rejection rule is satisfied. Control circuit 80 may set a flag or logic signal indicating so at block 430. Methods for determining gross morphology parameters and whether or not the gross morphology rejection rule is satisfied are described below in conjunction with FIGS. 14 through 19.

At block 422 a morphology matching score is determined from the stored, second cardiac electrical signal segment. The morphology matching score may be determined by performing wavelet transform or other morphology matching analysis on a portion of the stored segment, e.g., on at least 48 signal sample points or about 190 ms, and may be performed using the notch filtered signal produced at block 416. The morphology matching analysis may include aligning a selected portion of the stored segment with a previously-determined known R-wave template and determining a morphology matching score. The morphology matching score may have a possible range of values from 0 to 100 and indicates how well the morphology of the second cardiac signal segment matches the known R-wave template. A wavelet transform method as generally disclosed in U.S. Pat. No. 6,393,316 (Gillberg et al.) is one example of a morphology matching method that may be performed at block 422 for determining a matching score.

Other morphology matching methods that may be implemented by tachyarrhythmia detector 92 may compare the wave shape, amplitudes, slopes, inflection time points, number of peaks, or other features of the stored second cardiac electrical signal to a known R-wave template. More specifically, waveform duration or width, waveform polarity, waveform positive-going slope, waveform negative-going slope, and/or other waveform features may be used alone or in combination to characterize the similarity between the unknown waveform and a known R-wave template. Morphology matching methods may use one or a combination of two or more morphology features of the stored second cardiac electrical signal for determining a match to a known R-wave template. A posture-independent method for determining a morphology match score may be performed that includes generating posture-independent R-wave templates for use in template matching as generally disclosed in pre-grant U.S. Pat. Publication No. 2016/0022166 (Stadler, et al.), incorporated herein by reference in its entirety. Other beat morphology matching techniques that may be used at block 422 are generally disclosed in U.S. Pat. No. 8,825,145 (Zhang, et al.) and U.S. Pat. No. 8,983,586 (Zhang et al.), both incorporated herein by reference in their entirety.

The morphology matching score is used at block 432 by tachyarrhythmia detector 92 to update a beat morphology rejection rule. The beat morphology rejection rule may be satisfied when a minimum number of morphology match scores out of a predetermined number of most recent morphology match scores exceed a match score threshold in one example. For example, if at least three out of 8 of the most recent morphology match scores exceed a match score threshold of 50, 60, 70 or other score threshold, the beat morphology rejection rule is satisfied. A relatively high match score, exceeding a selected match score threshold, indicates the unknown beat matches the known R-wave template and is therefore a normal R-wave rather than a VT or VF beat. As such, when a threshold number of the most recent morphology match scores are determined to be normal R-waves, the beat morphology rejection rule is satisfied, and control circuit 80 may set a flag or logic signal indicating so.

The beat morphology rejection rule differs from the gross morphology rejection rule in that the beat morphology rejection rule is based on an analysis of the suspected R-wave signal to determine how likely it is to be normal R-wave. In other words the beat morphology rejection rule is applied to withhold a VT or VF detection based on verifying normal ventricular beats (or at least identifying beats that are not likely VT or VF beats). The gross morphology rejection rule is based on an analysis of a longer time interval of the signal segment than the beat morphology rejection rule so that a signal morphology parameter correlated to non-cardiac noise pulses, e.g., during the baseline portion of the second cardiac electrical signal may be detected. The gross morphology rejection rule is applied to withhold a VT or VF detection based on detecting noisy signal segments that may be interfering with reliable VT or VF detection or leading to a false VT or VF detection.

At block 424, TWOS parameters are determined from a stored, digitized cardiac electrical signal. In some cases, the TWOS parameters are determined from a first order differential signal 69 received from first sensing channel 83 as described in conjunction with FIG. 5 above. The first order differential signal is determined by subtracting the amplitude of the n−1 sample point from the nth sample point. Alternatively or additionally, the second cardiac electrical signal from sensing channel 85, before or after notch filtering, may be used for determining TWOS parameters for detecting TWOS based on morphology analysis of the stored cardiac signal, e.g., as generally disclosed in the above-incorporated U.S. Pat. Application No. 62/367,221. Tachyarrhythmia detector 92 may be configured to execute T-wave oversensing rejection algorithms by determining a differential filtered cardiac electrical signal and TWOS parameters as generally disclosed in the above-incorporated U.S. Pat. No. 7,831,304 (Cao, et al). Other aspects of detecting TWOS that may be used for determining TWOS parameters from the either the first and/or second cardiac electrical signal are generally disclosed in U.S. Pat. No. 8,886,296 (Patel, et al.) and U.S. Pat. No. 8,914,106 (Charlton, et al.), both incorporated herein by reference in their entirety.

At block 434, the TWOS parameter(s) determined for the currently stored cardiac signal segment are used by the tachyarrhythmia detector 92 to update the status of a TWOS rejection rule as being either satisfied or unsatisfied. For example, if one or more TWOS parameters indicate the R-wave sensed event signal produced by the first sensing channel 83 is likely to be an oversensed T-wave, a TWOS event counter may be updated at block 434. If the TWOS event counter reaches a threshold, the TWOS rejection rule is satisfied. Control circuit 80 may set a flag or logic signal indicating when the TWOS rejection rule is satisfied.

Other noise parameters may be determined at block 426 to identify oversensing due to noise artifacts. The noise parameters determined at block 426 may include determining peak amplitudes from the notch-filtered second cardiac electrical signal segment. All or a portion of the stored signal segment may be used for determining one or more amplitude peaks. In other examples, the first cardiac electrical signal segment may undergo notch filtering and be used for determining noise parameters at bock 426. The peak amplitudes determined at block 426 may include the maximum peak amplitude determined at block 418 for use in determining the amplitude ratio. The maximum peak amplitudes for one or more stored cardiac signal segments are compared to noise detection criteria for determining whether the noise rejection rule is satisfied at block 436. Control circuit 80 sets a flag or logic signal to indicate the status of the noise rejection rule at block 436. Methods for determining noise parameters at block 426 and updating a noise rejection rule at block 436 are generally disclosed in U.S. Pat. Application No. 62/367,170, incorporated herein by reference in its entirety.

After adjusting the VT and VF interval counters at block 112, the tachyarrhythmia detector 92 compares the interval counters to VT and VF NID detection thresholds at block 132. If the NID has been reached by either the VT or VF interval counter, tachyarrhythmia detector 92 checks the status of the rejection rules at block 440. If rejection criteria are satisfied at block 440, "yes" branch of block 440, based on the status of one or more rejection rules, the VT or VF detection based on RRI analysis at blocks 110, 112, and 132 is withheld at block 140. No VT or VF therapy is delivered. The process returns to block 110 to determine the next RRI upon receiving the next R-wave sensed event signal from sensing channel 83.

If the rejection criteria are not satisfied, "no" branch of block 440, the VT or VF episode is detected at block 136 according to which VT or VF interval counter reached its respective NID threshold. Control circuit 80 controls therapy delivery circuit 84 to deliver a therapy at block 138 according to the type of episode detected and programmed therapy delivery control parameters.

In some examples, the rejection criteria applied at block 440 require only a single rejection rule be satisfied in order to cause the tachyarrhythmia detector 92 to withhold a VT or VF detection. In other examples, two or more rejection rules may be required to be satisfied before an RRI-based VT or VF detection is withheld. In still other examples, one rejection rule may be linked with another rejection rule in order to have rejection criteria satisfied at block 440. For instance, the R-wave confirmation rejection rule may only be used to satisfy the rejection criteria when the gross morphology rejection rule is also satisfied. In this case, the R-wave confirmation rejection rule alone may not be used to satisfy the rejection criteria at block 440. The gross morphology rejection rule may be used only with the R-wave confirmation rejection rule, alone or in combination with another rule to satisfy the rejection criteria.

The rejection rules updated at blocks 428 through 436 may be programmably enabled or disabled by a user using external device 40. Control circuit 80 may determine which parameters are determined at blocks 418 through 426 as required for updating the status of only the rejection rules that are enabled or programmed "ON."

Figure 11:
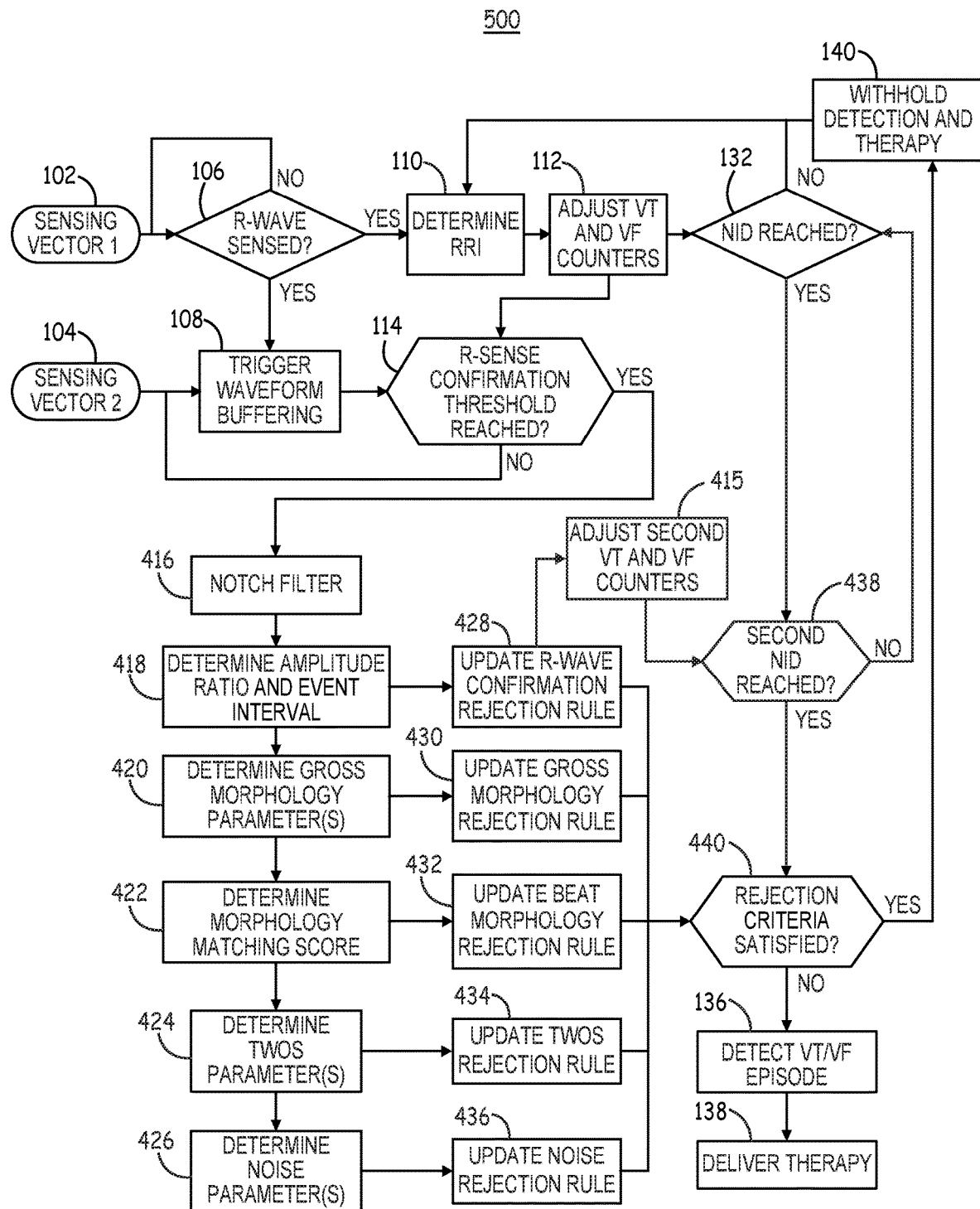
FIG. 11 is a flow chart of a method for detecting tachyarrhythmia by an ICD according to another example.

FIG. 11 is a flow chart 500 of a method for detecting tachyarrhythmia by ICD 14 according to another example. In the examples of FIG. 7 and FIG. 10, the number of RRIs determined from the first sensing electrode vector 102 that fall into a respective VT or VF interval range or zone are tracked by respective VT and VF interval counters. The counts of the VT and VF interval counters are compared to respective VT and VF NID thresholds at block 132. Identically-numbered blocks in FIG. 11 correspond to like-numbered blocks shown in FIGS. 7 and 10 as described above.

In other examples, the second cardiac electrical signal received by the second sensing channel 85 from the second electrode vector at block 104 may also be used for determining RRIs and determining whether an NID threshold is reached at decision block 438. Tachyarrhythmia detector 92 may include second VT and VF interval counters for counting RRIs determined from the second cardiac electrical signal received by the second sensing channel 85. The second VT and VF interval counters may be updated at block 415 based on RRIs determined from the second cardiac electrical signal received via the second sensing electrode vector 104.

In one instance, the tachyarrhythmia detector 92 may begin updating second VT and VF interval counters at block 415 after the R-sense confirmation threshold is reached at block 114. The process of updating the second VT and VF interval counters from an initialized zero count may include confirming an R-wave at block 428 based on comparing an amplitude ratio to a ratio threshold as described in conjunction with blocks 122, 124, 126, and 128 of FIG. 7. If the R-wave sense is confirmed at block 126, the R-wave confirmation rejection rule is updated at block 428 based on the confirmed R-wave sensed event, and tachyarrhythmia detector 92 compares the event interval determined at block 418 to VT and VF interval zones at block 415. The event interval determined at block 418 is the time interval from the most recently confirmed R-wave event time to the event time of the maximum absolute amplitude of the time segment stored for the most recent R-wave sensed event signal.

If the most recent R-wave sensed event signal is confirmed at block 428, the event interval may be compared at block 415 to VT and VF interval zones defined to be the same as the interval zones applied at block 112 to RRIs determined from R-wave sensed event signals produced by the first sensing channel 83. If the event interval determined at block 418 for a confirmed R-wave falls into the VT interval zone, the second VT interval counter is increased at block 415. If the event interval falls into the VF interval zone, the second VF interval counter is increased at block 415. In some examples, a combined VT/VF interval counter is increased if the event interval falls into either a VT or VF interval zone.

If one of the first VT or VF interval counters (or a combined VT/VF interval counter) applied to RRIs determined from the first sensing channel 83 reaches an NID at block 132, tachyarrhythmia detector 92 may compare the second VT and VF interval counters to second NID requirements at block 438. The second VT NID and the second VF NID used by tachyarrhythmia detector 92 may be less than the VT NID and VF NID applied to the first VT and VF interval counters at block 132. The second VT and VF interval counters begin to be updated after the R-sense confirmation threshold is reached at block 114 in some examples. As such, the second VT and VF interval counters may have counts that are less than the first VT and VF interval counters (that are adjusted at block 112). The counts of the second VT and VF interval counters may fall behind the first VT and VF interval counts by the number of intervals required to reach the R-sense confirmation threshold. For example, if a first VT interval counter is required to have a count of at least 2 or the first VF interval counter is required to have a count of at least 3 in order for the R-sense confirmation threshold to be reached at block 114, the second VT or VF interval counter may have a count that is at least 2 or 3, respectively, less than the first respective VT or VF interval counter.

If a second NID is reached by one of the second VT or VF interval counters, "yes" branch of block 438, tachyarrhythmia detector 92 determines if rejection criteria are met at block 440 based on the status of the rejection rules updated at block 428 through 436 as described above in conjunction with FIG. 10. If the second NID is not reached at block 438 by neither of the second VT or VF interval counters, "no" branch of block 438, tachyarrhythmia detector 92 does not advance to checking the rejection criteria at block 440. Rather, tachyarrhythmia detector 92 may wait for the first VT or VF NID to be reached at block 132 by the respective first VT or VF interval counter and for the respective second NID to be reached at block 438 by the respective second VT or VF interval counter. For instance, in order to advance to block 440 to determine if rejection criteria are satisfied and subsequently either detect VT at block 136 or withhold a VT detection at block 140, the first VT interval counter is required to reach the first VT NID at block 132 and the second VT interval counter is required to reach the second VT NID at block 438. Similarly, in order to advance to block 440 to determine if rejection criteria are satisfied and subsequently either detect VF at block 136 or withhold a VF detection at block 140, the first VF interval counter is required to reach the first VF NID at block 132 and the second VF interval counter is required to reach the second VF NID at block 438.

Figure 12:
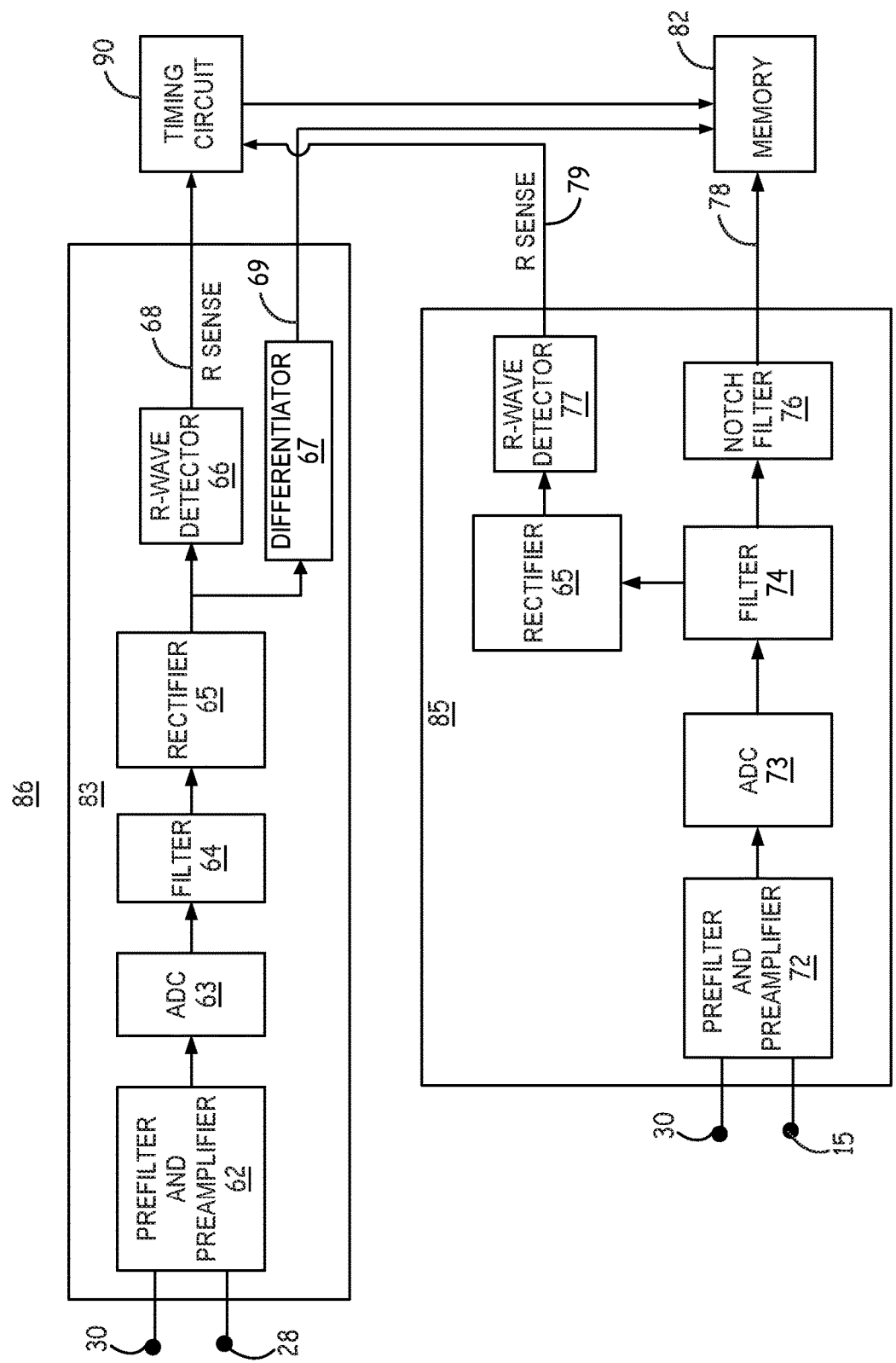
FIG. 12 is a diagram of circuitry included in the sensing circuit of FIG. 4 according to another example.

FIG. 12 is a diagram of circuitry included in the sensing circuit of FIG. 4 according to another example. In FIG. 12, identically-numbered components of sensing channels 83 and 85 correspond to like-numbered components described in conjunction with and shown in FIG. 5. In the example of FIG. 5, first sensing channel 83 is configured to sense R-waves by R-wave detector 66 in real time and produce R-wave sensed event signals 68 that are passed to timing circuit 90 as the R-waves are sensed. Second sensing channel 85 is configured to pass the filtered, digitized output signal 78 to memory 82 for storage of second cardiac electrical signal segments as triggered by R-wave sensed event signals 68 from first sensing channel 83 without performing real-time R-wave sensing from the second cardiac electrical signal.

In the example of FIG. 12, second sensing channel 85 is configured to pass the digitized filtered output signal 78 to memory 82 for storage of second cardiac electrical signal segments as described above. Sensing channel 85 is additionally configured to perform real-time R-wave sensing from the second cardiac electrical signal. In this case, second sensing channel 85 includes rectifier 75 for rectifying the digitized and bandpass filtered signal output of filter 74. The rectified signal is passed from rectifier 75 to R-wave detector 77. R-wave detector may include a sense amplifier, comparator or other R-wave detection circuitry configured to apply an auto-adjusting R-wave sensing threshold to the rectified signal for sensing an R-wave in response to a positive-going R-wave sensing threshold crossing.

Second sensing channel 85 may produce R-wave sensed event signals 79 that are passed to timing circuit 90 in real time for use in determining RRIs based on the second cardiac electrical signal. RRIs may be determined as the time interval or sample point count between consecutively received R-wave sensed event signals 79. Timing circuit 90 may pass RRIs determined from R-wave sensed event signals 79 from second sensing channel 85 to tachyarrhythmia detector 92 for use in updating second VT and VF interval counters based on RRIs determined from real-time sensing of R-waves by the second sensing channel 85.

In the flow chart 500 of FIG. 11, second VT and VF interval counters are updated at block 415 by tachyarrhythmia detector 92 based on R-waves confirmed at block 428 as a result of post-processing of the stored second cardiac electrical signal segments. R-waves are not sensed by the second sensing channel 85 in real time in the example of FIG. 11 (the signal segments may be recorded but R-wave sense event signals are not produced in real time as R-waves are sensed based on an R-wave sensing threshold). In FIG. 12, the second sensing channel 85 is configured to sense R-waves in real time from the second cardiac electrical signal received via the second sensing vector 104, and, as such, tachyarrhythmia detector 92 may update second VT and VF interval counters based on real-time sensing of R-waves by the second sensing channel 85.

Figure 13:
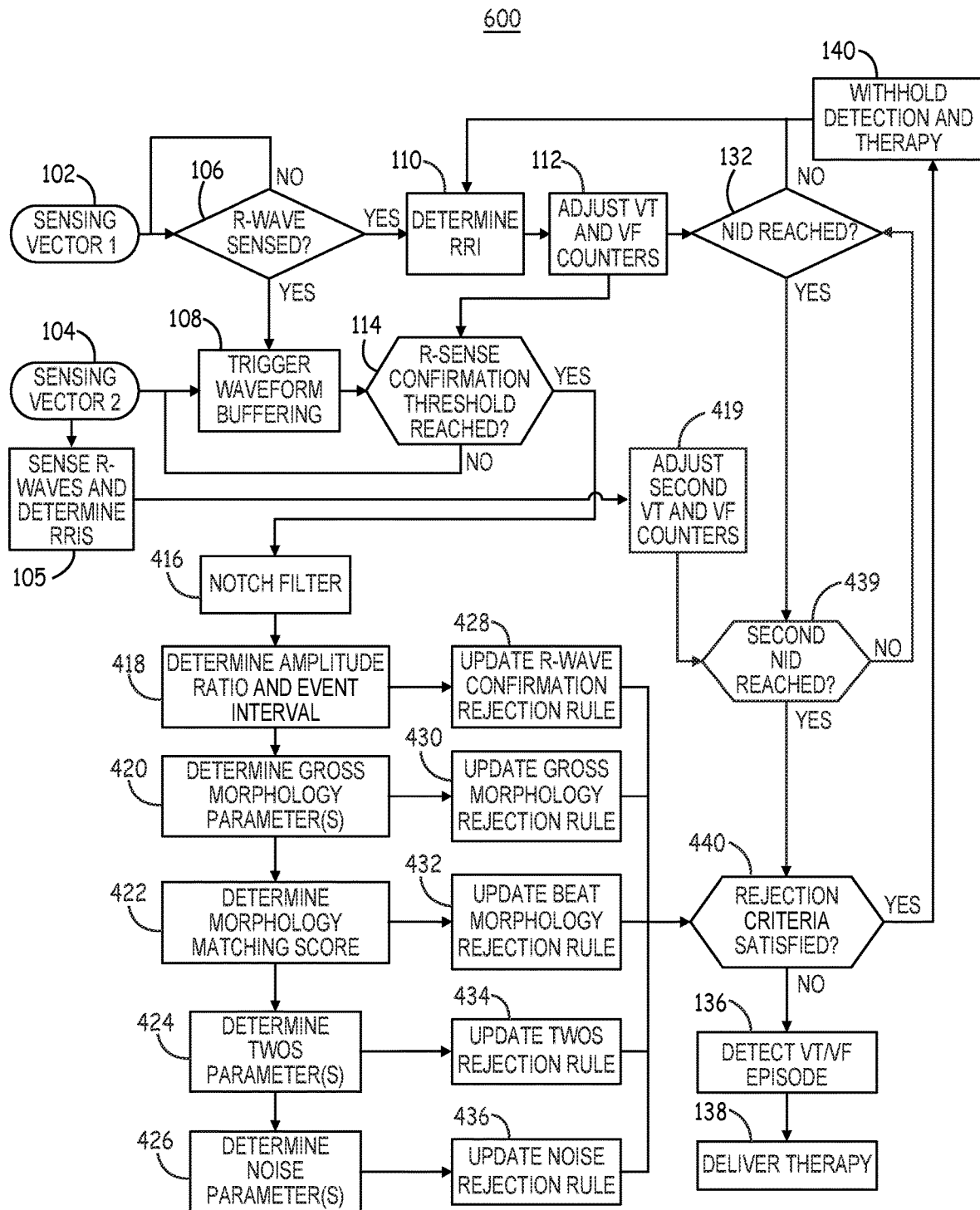
FIG. 13 is a flow chart of a method for detecting tachyarrhythmia by an ICD according to yet another example.

FIG. 13 is a flow chart 550 of a method for detecting tachyarrhythmia by ICD 14 according to another example in which the second sensing channel 85 is configured for real-time sensing of R-waves from the second cardiac electrical signal in addition to the control circuit 80 being configured to confirm R-waves sensed by the first sensing channel 83 by post-processing of the second cardiac electrical signal. Identically-numbered blocks in FIG. 13 correspond to like-numbered blocks shown in FIGS. 7 and/or 11 and described in conjunction therewith.

In the example of FIG. 13, at block 105, R-wave detector 77 of sensing channel 85 produces R-wave sensed event signals 79 (shown in FIG. 12), e.g., in response to crossings of a second R-wave sensing threshold by the second cardiac electrical signal. The second R-wave sensing threshold may be an auto-adjusting threshold and may be different than the R-wave sensing threshold used by R-wave detector 66 of the first sensing channel 83. Timing circuit 90 determines RRIs between consecutive R-wave sensed event signals 79 received from second sensing channel 85 at block 105 and passes the determined RRIs to tachyarrhythmia detector 92. At block 419, tachyarrhythmia detector 92 adjusts the second VT interval counter or the second VF interval counter, which may both be X of Y type counters, in response to each RRI determined at block 105. In this example, the second VT and VF interval counters of tachyarrhythmia detector 92 may be updated in real time, similar to the first VT and VF interval counters used to count RRIs determined from the first cardiac electrical signal. The second VT and VF interval counters may be updated on a beat-by-beat basis without requiring the R-sense confirmation threshold to be reached first (block 114).

If the tachyarrhythmia detector 92 determines that a first VT NID or first VF NID is reached at block 132, the tachyarrhythmia detector 92 compares the second VT and VF interval counters to a second VT NID and second VF NID, respectively, at block 439. In this case, the second VT NID and second VF NID may be the same as the first VT NID and the first VF NID since all of the first and second VT interval counters and the first and second VF interval counters are being updated in response to R-waves that are sensed in real time. If the second VT or VF NID has not been reached ("no" branch of block 430), the tachyarrhythmia detector 92 may return to block 132 to wait for the VT or VF NID thresholds to be reached based on R-waves sensed in real time by both the respective first and second sensing channels 83 and 85.

If a second VT or VF NID is reached at block 439 when a corresponding first VT or VF NID is reached at block 132, the tachyarrhythmia detector 92 determines if rejection criteria are satisfied at block 440 as described previously in conjunction with FIG. 10. A pending VT of VF detection based on tachyarrhythmia intervals being detected in real time from both the first and second cardiac electrical signals is either withheld at block 140 in response to rejection criteria being met or the VT or VF detection is confirmed at block 135 if the rejection criteria are not satisfied. Control circuit 80 controls the therapy delivery circuit to deliver an anti-tachyarrhythmia therapy at block 138 in response to the VT or VF detection.

Figure 14:
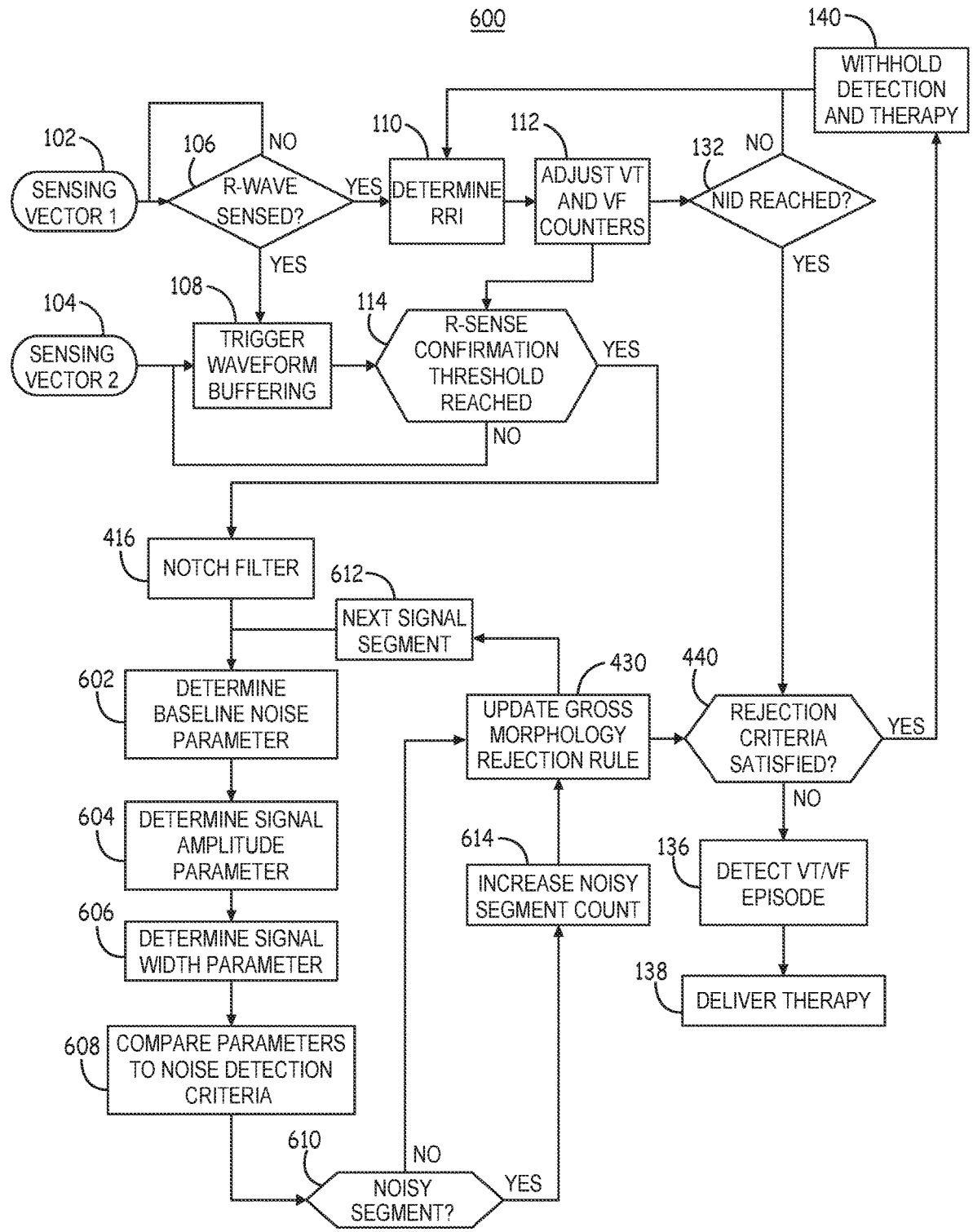
FIG. 14 is a flow chart of a method performed by an ICD for withholding a ventricular tachyarrhythmia detection in response to a gross morphology rejection rule.

FIG. 14 is a flow chart 600 of a method performed by ICD 14 for withholding a VT or VF detection in response to the gross morphology rejection rule (block 430, FIGS. 10, 11 and 13) being satisfied. Blocks 102 through 114, 132, 136, 138, and 140 of FIG. 14 correspond to identically-numbered blocks described above in conjunction with FIGS. 10, 11 and 13.

As described above, if the R-sense confirmation threshold is reached at block 114, the control circuit 80 applies a notch filter to the stored, second cardiac electrical signal segment at block 416. The notch filter applied at block 416 may correspond to the filter described in conjunction with FIG. 6. The notch-filtered, second cardiac electrical signal segments are used at blocks 602, 604 and 606 to determine morphology parameters relating to baseline noise (block 602), maximum signal amplitude (block 604) and maximum signal width (block 606). Examples of methods that may be performed by control circuit 80 for determining a baseline noise parameter, determining a signal amplitude parameter, and determining a signal width parameter are described below in conjunction with FIGS. 15, 16 and 17, respectively. The methods performed at blocks 602, 604 and 608 may correspond to the determination of gross morphology parameters at block 420 of FIGS. 10, 11 and 13.

These parameters are compared to noise detection criteria at block 608. If the noise detection criteria are satisfied at block 608, the second cardiac signal segment being analyzed is determined to be a noisy segment at block 610. The noise contamination of the signal segment may be caused by muscle (myoelectric) noise, EMI or other non-cardiac electrical noise sources.

In response to detecting a noisy segment at block 610 ("yes" branch), control circuit 80 increases a noisy segment count at block 614 to track the number of segments identified as being noisy based on the morphology parameters after the R-wave confirmation threshold is reached at block 114. The status of the gross morphology rejection rule is updated at block 430 based on the value of the noisy segment count. When the segment is not detected as being noisy, "no" branch of block 610, the gross morphology rejection rule may be updated at block 430 to track the number of noisy segments that are detected out of a predetermined number of segments analyzed or out of the most recent R-wave sensed event signals. The gross morphology rejection rule may be satisfied based on the noisy segment count value. If a threshold number of noisy segments are detected, the rejection rule is satisfied at block 430. For example, if at least two out of the most recent eight (or other predetermined number) analyzed cardiac electrical signal segments are classified as noisy, the rejection rule is updated as being satisfied at block 430. If less than two out of the most recent eight analyzed cardiac electrical signal segments are classified as noisy, the rejection rules are updated as being unsatisfied.

The next signal segment is fetched at block 612 and undergoes the same analysis at blocks 602 through 610 to determine whether the segment is noisy or not based on the noise detection criteria applied at block 608. As described below in conjunction with FIG. 19, the next signal segment to undergo analysis for detecting a noisy signal segment may not correspond to the next consecutive R-wave sensed event signal. In some cases, the next signal segment that is fetched at block 612 corresponds to an R-wave sensed event signal that occurs at least 300 ms or another predetermined time limit after the R-wave sensed event signal that triggered storage of the signal segment currently being analyzed. In this way, signal segments analyzed for being identified as noisy signal segments may sometimes be consecutive and at other times be non-consecutive. R-wave sensed event signals that occur at an RRI less than the predetermined time limit may be skipped for the purposes of determining gross morphology parameters. In other examples, each R-wave sensed event signal that occurs outside of the post-sense blanking interval is analyzed for determining gross morphology parameters.

In response to the NID being reached at block 132, based on RRIs determined from the cardiac electrical signal received via the first sensing vector 102 by the first sensing channel 83, control circuit 80 determines if rejection criteria are satisfied at block 440. In the example of FIG. 14, control circuit 80 checks the status of the gross morphology rejection rule updated at block 430. If the gross morphology rejection rule is satisfied when the NID is reached at block 132, e.g., if at least two out of the most recent eight signal segments analyzed, as given in the example above, are detected as noisy segments, a VT or VF detection based on the NID being reached at block 132 is withheld at block 140; no therapy is delivered.

This process of analyzing signal segments for detecting noisy segments may be repeated as long as the R-sense confirmation threshold is still being met or until a VT or VF is detected. VT or VF is detected at block 136 when the NID is reached and the gross morphology rejection rule (and any other rejection rules applied at block 440 as described previously herein) is not satisfied ("no" branch of block 440). Control circuit 80 controls therapy delivery circuit 84 to deliver a therapy, e.g., ATP or a shock therapy, according to programmed therapies. It is to be understood that in some examples, the VT or VF detection made at block 136 may require a second NID to be reached based on RRIs determined from the second cardiac electrical signal as described in conjunction with FIGS. 11 and 13.

FIG. 15 is a flow chart 700 of a method performed by ICD 14 for determining a morphology parameter correlated to baseline noise at block 602 of FIG. 14 according to one example. The morphology parameter correlated to baseline noise is referred to herein as a baseline noise parameter and in the example of FIG. 15 the morphology parameter correlated to baseline noise is a count of signal pulses during the signal segment.

At block 702 a first order differential signal may be determined from the notch-filtered second cardiac electrical signal segment. In one example, the stored segment is at least 360 ms long so that a first order differential signal is determined using sample points over a 360 ms segment of the second cardiac electrical signal, e.g., after notch-filtering. The 360 ms segment may include sample points preceding and following an R-wave sensed event signal. For instance, the 360 ms segment may include 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal. By processing relatively fewer sample points occurring after the R-wave sensed event signal, control circuit 80 does not need to wait long after the R-wave sensed event signal for acquiring all sample points needed to determine the baseline noise parameter (and other gross morphology parameters), thereby minimizing the signal processing delay in detecting noise and updating the gross morphology rejection rule. The first order differential signal is computed by computing successive differences, $A(n)-A(n-1)$, between sample points, where n is the sample point number, ranging from 1 to 92 in the example given above, $A(n)$ is the amplitude of the nth sample point and $A(n-1)$ is the amplitude of the immediately preceding n−1 sample point.

At block 704, zero crossings are set by identifying consecutive sample points of the differential signal having opposite polarity. For example, a positive sample point followed by a negative sample point is identified as a zero crossing, or a negative sample point followed by a positive sample point is identified as a zero crossing. Control circuit 80 compares the absolute values of the two signal sample points identified as a zero crossing. The sample point of the differential signal having the smaller absolute value amplitude is set to zero amplitude to clearly demark each zero crossing with two consecutive zero crossings defining a baseline noise pulse.

The differential signal with zero crossings set is rectified at block 706. At block 708, a noise pulse amplitude threshold is determined. The noise pulse amplitude threshold may be determined based on the maximum amplitude of the rectified differential signal over the entire segment being analyzed, over 360 ms in the example given above. The noise pulse amplitude threshold may be set to a portion or percentage of the maximum amplitude of the rectified differential signal. For instance, the noise pulse amplitude threshold may be set to be one-eighth of the maximum amplitude of the rectified differential signal.

At block 710, signal pulses within the segment being analyzed are identified and counted. Signal pulses are identified by comparing the sample point amplitudes of the rectified differential signal occurring between two consecutive zero crossings to the noise pulse amplitude threshold. If the rectified differential signal amplitude crosses the noise pulse amplitude threshold, a signal pulse is identified and counted at block 710. The control circuit 80 may advance through the entire stored signal segment, or selected portion thereof that extends earlier in time than the QRS complex to include a baseline signal portion, to identify and count all pulses exceeding the noise pulse amplitude threshold in the segment under analysis. The baseline noise parameter determined at block 602 of FIG. 14 is the count of identified signal pulses determined at block 710. Other techniques that may be implemented for determining a baseline noise parameter at block 602, such as a muscle noise pulse count, are generally disclosed in U.S. Pat. No. 8,435,185 (Ghanem, et al.), incorporated herein by reference in its entirety.

Figure 16:
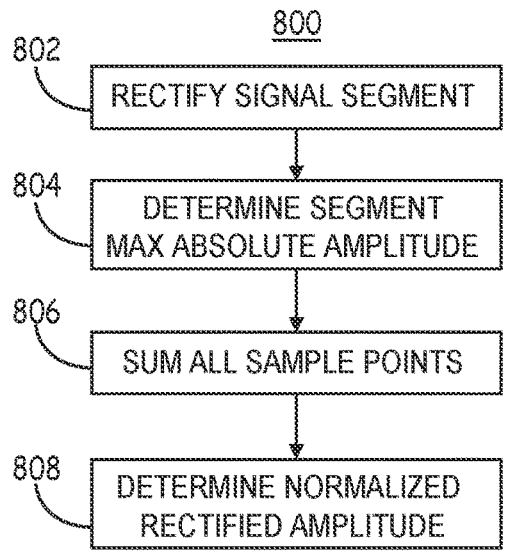

FIG. 16 is a flow chart 800 of a method for determining an amplitude parameter at block 605 of FIG. 14 according to one example. At block 802, the notch-filtered signal segment is rectified, e.g., a 360 ms segment as described above in conjunction with FIG. 15 is rectified. Control circuit 80 determines the maximum absolute amplitude of the rectified, notch-filtered segment at block 804. The amplitudes of all sample points of the rectified signal segment under analysis are summed at block 806. At block 808, the normalized rectified amplitude (NRA) is determined based on the maximum absolute amplitude determined at block 804 and the summed sample point amplitudes determined at block 806. In one example, the NRA is determined as the ratio of a predetermined multiple of the summation of all sample point amplitudes of the notch-filtered and rectified signal segment to the maximum absolute amplitude. For instance, the NRA may be determined as four times the summed amplitudes divided by the maximum absolute amplitude, which may be truncated to an integer value. This NRA may be determined as the amplitude parameter at block 604 of FIG. 14. The higher this amplitude parameter value is, the more likely that the signal segment contains a valid R-wave of a VT or VF episode. The signal segment may be identified as a "shockable beat" when the amplitude parameter is greater than a shockable beat amplitude threshold as described below in conjunction with FIG. 18.

Figure 17:
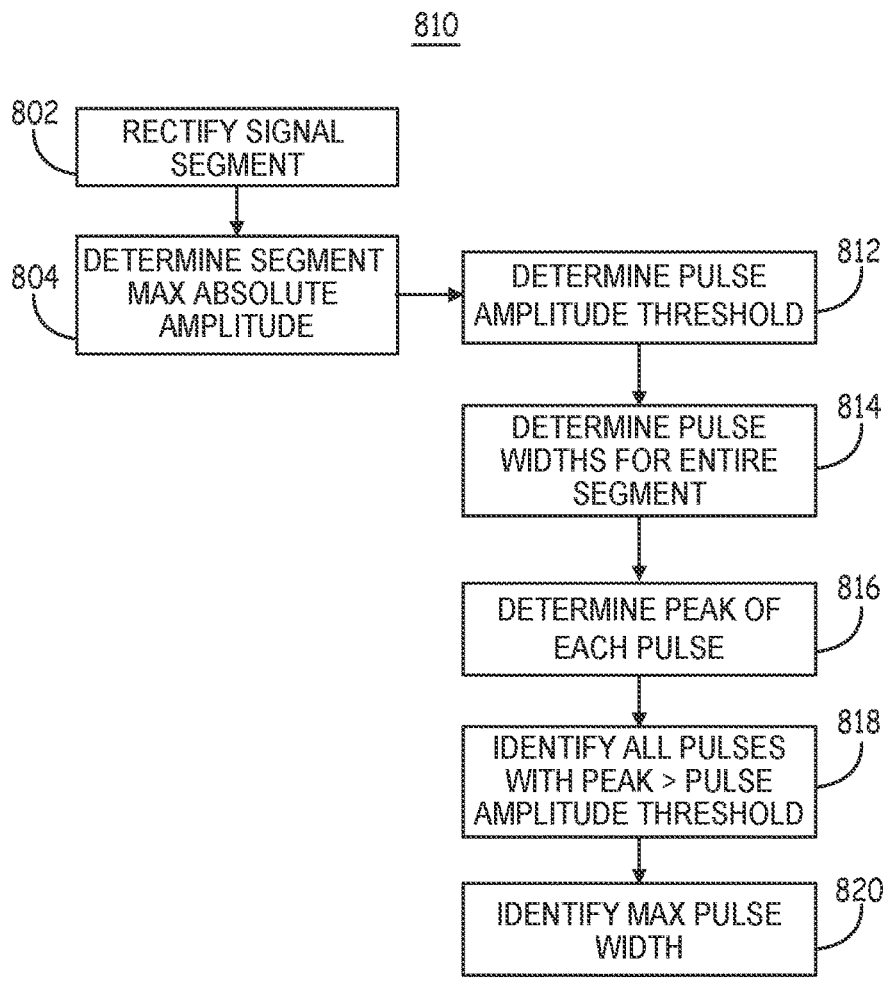

FIG. 17 is a flow chart 810 of a method that may be performed by control circuit 80 for determining a signal width parameter at block 606 of FIG. 14. Blocks 802 and 804 correspond to identically-numbered blocks described above in conjunction with FIG. 16. The notch-filtered, rectified signal segment determined at block 802 and the maximum absolute amplitude of the rectified signal segment determined at block 804 are used for determining the signal amplitude parameter at block 604 of FIG. 14 and the signal width parameter at block 606 of FIG. 14. In other examples, however, the differential signal with set zero crossings used to determine the pulse count as described in conjunction with FIG. 15 may also be used to determine the signal amplitude and signal width parameters instead of the notch-filtered, rectified signal segment.

Control circuit 80 determines a pulse amplitude threshold at block 812 based on the maximum absolute amplitude. This pulse amplitude threshold is used for identifying a signal pulse having the maximum signal width in the second cardiac electrical signal segment. The pulse amplitude threshold determined at block 812 may be a different threshold than the noise pulse amplitude threshold determined at block 708 of FIG. 15. For example, the pulse amplitude threshold used for determining the signal width parameter may be set to half the maximum absolute amplitude of the rectified, notch-filtered signal segment whereas the noise pulse amplitude threshold used in FIG. 15 to determine a count of signal pulses may be set to one-eighth the maximum amplitude of rectified, differential signal segment.

The signal amplitude parameter determined by the method of FIG. 16 and the signal width parameter determined by the method of FIG. 17 are used to identify signal pulses that are more likely to be an R-wave of a potential VT or VF rhythm than a baseline noise pulse. A signal segment that has a relatively large signal amplitude parameter and/or relatively large signal width parameter is potentially a heartbeat of a VT or VF rhythm rather than noise, and is referred to herein as a "potential shockable beat." When a potential shockable beat is detected based on a large signal amplitude and/or signal width parameter, more stringent criteria may be applied for detecting the signal segment as a noisy segment to avoid withholding a VT or VF detection based on a potential shockable beat. The signal segment including a potential shockable beat is required to meet higher noise detection criteria in order to justify counting the signal segment as a noisy segment at block 614 (FIG. 14), which may lead toward satisfying the gross morphology rejection rule and withholding a VT or VF detection. Otherwise a potential shockable beat that is counted as a noisy segment based on less stringent noise detection criteria may lead to withholding or delay of a VT or VF detection during a true tachyarrhythmia episode.

At block 814, control circuit 80 determines the signal width for all pulses of the segment as the number of sample points (or corresponding time interval) between a pair of consecutive zero crossings of the rectified signal. The maximum peak of each pulse is determined at block 816. All pulses having a maximum peak that is greater than or equal to the pulse amplitude threshold determined at block 812, e.g., greater than half the maximum absolute amplitude, are identified. Of the pulses having a maximum peak amplitude that is at least the pulse amplitude threshold, the pulse having the greatest pulse width is identified at block 820. This maximum pulse width is determined as the signal width parameter at block 606 of FIG. 14.

Figure 18:
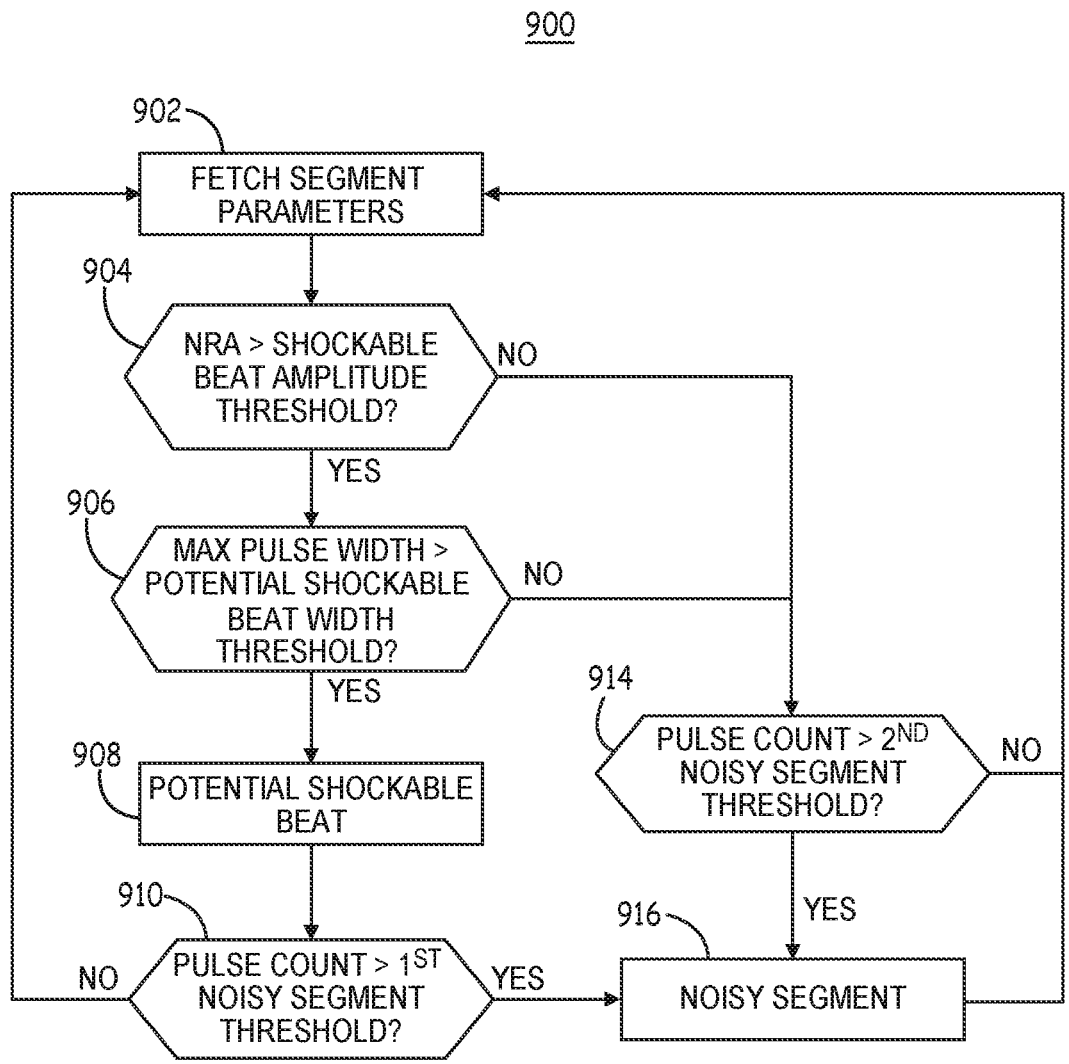
FIG. 18 is a flow chart of a method for comparing the gross morphology parameters of FIGS. 15, 16 and 17 to noisy segment detection criteria and detecting a cardiac electrical signal segment as a noisy segment.

FIG. 18 is a flow chart 900 of a method for comparing the gross morphology parameters to noise detection criteria and detecting the segment as a noisy segment. The process of flow chart 900 may be performed at blocks 608 and 610 of FIG. 14. At block 902, control circuit 80 fetches the gross morphology parameters determined at blocks 602, 604 and 606 for comparison to noise detection criteria. The NRA is compared to a potential shockable beat amplitude threshold at block 904. When the NRA is determined as described above in conjunction with FIG. 16, the potential shockable beat amplitude threshold may be set between 100 and 150, and to 140 in some examples. If the NRA is greater than the threshold, the signal segment may likely include a true R-wave of a VT or VF episode and is therefore a potential shockable beat (if it is occurring at a VT or VF interval).

At block 906, the maximum pulse width is compared to a potential shockable beat width threshold. If the NRA and the maximum pulse width for the signal segment are both greater than the respective amplitude and width thresholds at blocks 904 and 906, the segment is identified as a potential shockable beat at block 908. In one example, the potential shockable beat width threshold is set to 20 sample points when the sampling rate is 256 Hz. The signal pulse count determined as the baseline noise parameter (as described in conjunction with FIG. 15) is compared to a first noisy segment threshold at block 910. If the signal pulse count is greater than the noisy segment threshold, e.g., greater than 12, the segment is detected as a noisy segment at block 916. The noisy segment count is increased by one at block 614 of FIG. 14 in response to detecting the noisy segment.

If the pulse count is less than the first noisy segment threshold, "no" branch of block 910, the segment is not detected as a noisy segment, and the process returns to block 902 to fetch the gross morphology parameters for the next signal segment, as long as the R-sense confirmation threshold is still being reached at block 114 and VT or VF has not been detected.

If the segment is not identified as a potential shockable beat, "no" branch of block 904 or "no" branch of block 906, the count of identified signal pulses is compared to a second noisy segment threshold at block 914. The second noisy segment threshold may be lower than the first noisy segment threshold. If the segment is not identified as a potential shockable beat based on the amplitude parameter and the signal width parameter, less stringent criteria, e.g., a lower noisy segment threshold, may be applied for classifying the segment as a noisy segment. In one example, the second noisy segment threshold is six. If the pulse count exceeds the second noisy segment threshold, the segment is detected as a noisy segment at block 916 and will be counted by the control circuit 80 at block 614 of FIG. 14. Otherwise, the segment is not detected as a noisy segment ("no" branch of block 914), and the gross morphology parameters for the next segment are fetched at block 902.

The gross morphology rejection rule is satisfied when the value of the noisy segment count reaches or exceeds a rejection threshold, e.g., two noisy segments counted out of the eight most recent analyzed segments as described above in conjunction with FIG. 14. The segment is classified as noisy based on a count of signal pulses, positive- or negative-going in the originally stored segment, that have a differential signal absolute amplitude greater than a noise pulse amplitude threshold. In the example of FIG. 18, the number of signal pulses required to detect a noisy segment is smaller when the segment is identified as a potential shockable beat based on a relatively large amplitude parameter and/or a relatively large signal width parameter than the number of signal pulses required to detect a noisy segment when the segment is not identified as a potential shockable beat. In the example of FIG. 18, both the amplitude parameter and the signal width parameter are required to exceed a respective amplitude threshold and width threshold in order to identify the segment as a potential shockable beat. In other examples, only one of the amplitude parameter or the signal width parameter may be required to exceed its respective threshold in order to identify the segment as a potential shockable beat.

Figure 19:
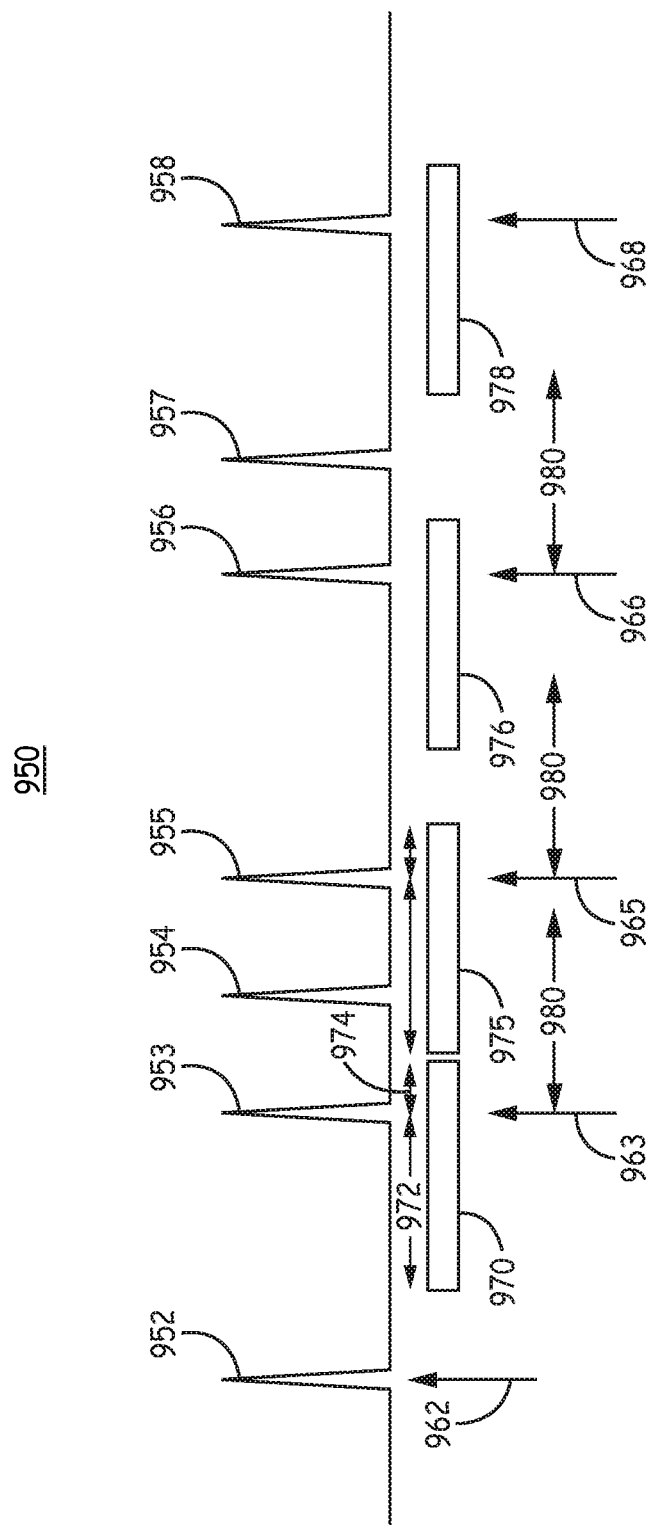
FIG. 19 is a timing diagram depicting time segments over which a morphology parameter correlated to baseline noise, an amplitude parameter and a signal width parameter may be determined for determining whether the respective time segment is a noisy segment.

FIG. 19 is a timing diagram 950 depicting time segments over which the morphology parameter correlated to baseline noise, amplitude parameter and signal width parameter may be determined. An R-wave sensed event signal 952 occurring at time 962 may cause the R-wave confirmation threshold to be reached. The next R-wave sensed event signal 953 at time 963 triggers storage of a time segment 970 of the second cardiac electrical signal segment. A portion 972 of the time segment 970 extends earlier than the R-wave sensed event signal 953 and a portion 974 extends after the R-wave sensed event signal 953. The gross morphology parameters may be determined for the time segment 970 and analyzed for determining if noise detection criteria are satisfied for detecting segment 970 as a noisy segment according to the methods of FIGS. 15 through 18.

The next R-wave sensed event signal 954 occurs within a predetermined time limit 980 from time 963. As such, analysis of a time segment corresponding to R-wave sensed event signal 954 is skipped in some examples. A second cardiac electrical signal segment may be stored for R-wave sensed event signal 954 and used in other signal analysis for use in confirming a sensed R-wave and/or determining the status of other rejection rules, but is not used in the gross morphology rejection rule analysis in some examples. Time limit 980 may be 300 ms in one example but may be longer or shorter than this value. The time limit 980 may be set to enable processing time of the analysis of a time segment 970 to be performed prior to starting analysis of the next time segment. The next R-wave sensed event signal 955 occurs at time 965, after time limit 980 expires. A time segment 975 buffered in memory 82 in response to R-wave sensed event signal 955 is analyzed for determining if it is a noisy segment.

R-wave sensed event 956 at time 966 occurs after time limit 980 expires, so time segment 976 of the second cardiac electrical signal is analyzed according to the methods of FIGS. 15-18. R-wave sensed event signal 957 occurs within the time limit 980 after R-wave sensed event signal 956 so analysis of a corresponding time segment is skipped according to the example of FIG. 19. The next time segment 978 corresponding to R-wave sensed event 958 at time 968 is the earliest occurring R-wave sensed event after time limit 980 expires and is therefore analyzed for determining if the segment 978 is a noisy segment. As such, time segments of the second cardiac electrical signal may sometimes correspond to consecutive R-wave sensed event signals and sometimes correspond to non-consecutive R-wave sensed event signals when one or more time segments corresponding to R-wave sensed events that occur within the predetermined time limit 980 are skipped.

Figure 20:
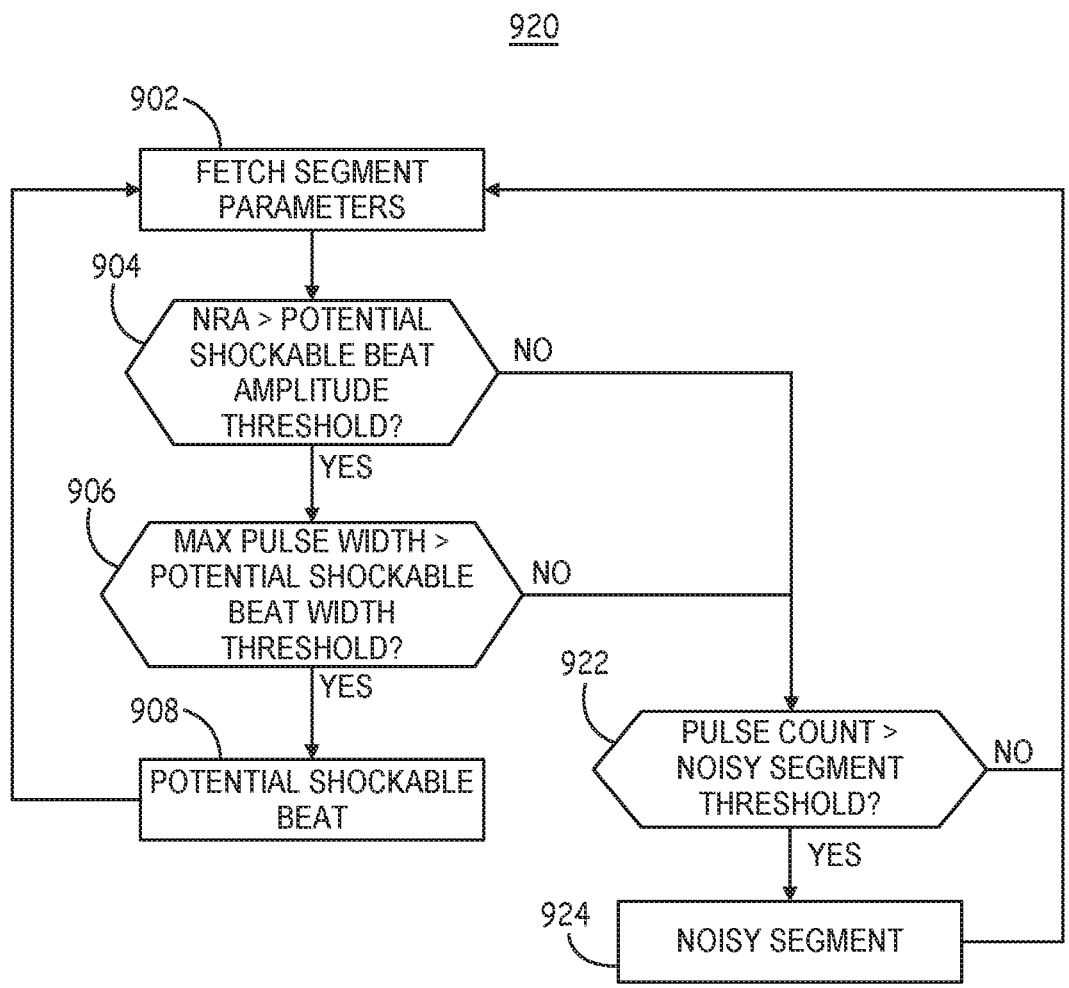
FIG. 20 is a flow chart of a method for comparing the gross morphology parameters to noise detection criteria and detecting the segment as a noisy segment according to another example.

FIG. 20 is a flow chart 920 of a method for comparing the gross morphology parameters to noise detection criteria and detecting the segment as a noisy segment according to another example. In some examples, each second cardiac electrical signal time segment corresponding to each R-wave sensed event signal received after the R-sense confirmation threshold is reached is analyzed without requiring that the R-wave sensed event signal occurs after a predetermined time limit as shown in FIG. 19. A post-sense blanking interval, e.g., blanking interval 214 of FIG. 8, may be applied after each R-wave sensed event signal, precluding an R-wave sensed event signal earlier than the post-sense blanking interval expiration. The post-sense blanking interval may be 150 ms for example. The second cardiac electrical signal segment buffered for each consecutive R-wave sensed event signal that occurs outside the post-sense blanking interval may be analyzed. In examples including a predetermined time limit 980 as shown in FIG. 19, the time limit 980 may be set to zero such that every R-wave sensed event signal after the post-sense blanking interval expires results in gross morphology analysis of the corresponding second cardiac electrical signal segment (after the R-sense confirmation threshold is reached).

Blocks 902 through 908 correspond to identically-numbered blocks of FIG. 18. The segment parameters are fetched at block 902, and the NRA and max pulse width are compared to respective shockable beat amplitude and width thresholds at blocks 904 and 906. If both the NRA and max pulse width are greater than their respective amplitude and width thresholds ("yes" branches of both blocks 904 and 906), the segment is classified as a potential shockable beat at block 908. In this example, no comparison is made to a noisy segment threshold when the segment is classified as a potential shockable beat. The segment does not cause the gross morphology rejection rule to be satisfied so that if the NID is reached (block 132 of FIG. 14), detection and therapy are not withheld. The process returns to block 902 to fetch the segment parameters for the next stored, second cardiac electrical signal segment if the R-sense confirmation threshold is still met and a VT or VF episode is not detected.

If one or both of the NRA and max pulse width are less than their respective thresholds ("no" branch of block 904 and/or block 906), the signal pulse count determined for the segment is compared to a noisy segment threshold at block 922. The noise segment threshold may be a pulse count of 8, 10, 12 or other predetermined threshold, which will depend in part on the duration of the signal segment being analyzed. If the pulse count is not greater than the noisy segment threshold, "no" branch, the segment is not classified as noisy and does not cause the noisy segment count to be increased at block 614 of FIG. 14. If the pulse count is greater than the noisy segment threshold, e.g., a pulse count of 12 or more, the segment is classified as a noisy segment at block 924. The noisy segment count is increased at block 614 of FIG. 14 and the gross morphology rejection rule status is updated at block 430. If the gross morphology rejection rule is satisfied, as determined at block 440, e.g., based on the noisy segment count reaching a threshold value such as at least two segments classified as noisy out of the most recent eight analyzed segments, the gross morphology rejection rule is satisfied. If the NID is reached based on the first cardiac electrical signal, the VT/VF detection is withheld, and therapy is withheld at block 140 of FIG. 14.

In the example of FIG. 18, a segment classified as a potential shockable beat could still be classified as a noisy segment based on a higher, more stringent pulse count threshold (block 910 of FIG. 18). In the example of FIG. 20, all second cardiac electrical signal segments that are identified as potential shockable beats based on the signal amplitude parameter and/or signal width parameter are not classified as noisy segments and do not lead to withholding of VT/VF detection and therapy. At least one or both of the amplitude and width parameters are required to be less than their respective potential shockable beat amplitude and width thresholds in order to make the comparison of the signal pulse count to the noisy segment threshold at block 922 and detect a noisy segment at block 924.

Thus, a method and apparatus for withholding a ventricular tachyarrhythmia detection in response to detecting noise contamination of cardiac electrical signal segments in an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A medical device system comprising:
    a sensing circuit comprising:
        a first sensing channel configured to receive a first cardiac electrical signal via a first sensing electrode vector coupled to the medical device system, the first sensing channel configured to sense R-waves in response to crossings of a sensing amplitude threshold by the first cardiac electrical signal, and
        a second sensing channel configured to receive a second cardiac electrical signal via a second sensing electrode vector coupled to the medical device system, the second sensing electrode vector being different than the first sensing electrode vector;
    a memory; and
    a control circuit coupled to the sensing circuit and the memory, the control circuit configured to:
        store a time segment of the second cardiac electrical signal in the memory in response to each one of a plurality of R-waves sensed by the first sensing channel from the first cardiac electrical signal;
        for each of the stored time segments,
            determine a morphology parameter correlated to signal noise from the stored time segment; and
            detect the stored time segment as being one of a noisy signal segment or a not noisy signal segment based on the morphology parameter determined for the respective stored time segment;
        detect a threshold number of the stored time segments as noisy signal segments; and
        withhold detection of a tachyarrhythmia episode in response to detecting at least the threshold number of the stored time segments as noisy signal segments.

2. The system of claim 1, further comprising a notch filter, wherein the time segments of the second cardiac electrical signal are filtered by the notch filter prior to determining the morphology parameter.

3. The system of claim 1, wherein the control circuit is further configured to:
    determine a plurality of intervals between successive ones of the R-waves sensed by the first sensing channel; and
    determine the morphology parameter from each of the stored time segments in response to at least a predetermined number of the plurality of intervals being less than a tachyarrhythmia detection interval.

4. The system of claim 1, wherein the control circuit is configured to determine the morphology parameter for each of the stored time segments by:
    identifying signal pulses occurring during the stored time segment of the second cardiac electrical signal; and
    determining a count of the identified signal pulses.

5. The system of claim 4, wherein the control circuit is configured to identify the signal pulses by:
    identifying zero crossings of the second cardiac electrical signal during the stored time segment;
    determining that the second cardiac electrical signal crosses a noise pulse amplitude threshold between two consecutive zero crossings; and
    identifying a signal pulse in response to the second cardiac electrical signal crossing the noise pulse amplitude threshold between two consecutive zero crossings.

6. The system of claim 1, wherein the control circuit is further configured to, for each of the stored time segments:

determine from the stored time segment at least one of a signal width parameter or a signal amplitude parameter;

detect a potential shockable beat based on at least one of the signal width parameter or the signal amplitude parameter;

compare the morphology parameter to a first noisy segment threshold in response to detecting the potential shockable beat;

determine that the morphology parameter determined for the stored time segment is greater than or equal to the first noisy segment threshold;

determine that the stored time segment is a noisy signal segment in response to the morphology parameter determined for the stored time segment being greater than or equal to the first noisy segment threshold.

7. The system of claim 6, wherein the control circuit is further configured to, for each of the stored time segments:

compare the morphology parameter to a second noisy segment threshold in response to not detecting a potential shockable beat based on the at least one of the signal width parameter or the signal amplitude parameter; and determine that the stored time segment is a noisy signal segment in response to the morphology parameter determined for the stored time segment being greater than or equal to the second noisy segment threshold, the second noisy segment threshold less than the first noisy segment threshold.

8. The system of claim 1, wherein the control circuit is further configured to, for each of the stored time segments:

determine from the stored time segment at least one of a signal width parameter or a signal amplitude parameter;

determine that the stored time segment is not a potential shockable beat based on at least one of the signal width parameter or the signal amplitude parameter;

compare the morphology parameter to a noisy segment threshold in response to determining the stored time segment is not a potential shockable beat; and determine that the stored time segment is a noisy signal segment in response to the morphology parameter determined for the stored time segment being greater than or equal to the noisy segment threshold.

9. The system of claim 8, wherein the control circuit is configured to determine the signal width parameter by:

identifying zero crossings of the second cardiac electrical signal during the stored time segment;

identifying a signal pulse in response to the second cardiac electrical signal crossing a pulse amplitude threshold between two consecutive zero crossings;

determining a pulse width of each identified signal pulse as a time interval between the two consecutive zero crossings of each respective identified signal pulse;

determining the signal width parameter as a maximum one of the determined pulse widths.

10. The system of claim 8, wherein the control circuit is further configured to:

determine the signal amplitude parameter by:
determining a summation of absolute amplitudes of all sample points of the stored time segment; and
normalizing the summation by a maximum sample point amplitude of the stored time segment;

compare the signal amplitude parameter to a shockable beat amplitude threshold;

determine that the signal amplitude parameter is greater than the shockable beat amplitude threshold;

compare the signal width parameter to a shockable beat width threshold;

determine that the signal width parameter is greater than the shockable beat width threshold; and detect the potential shockable beat when the signal amplitude parameter is greater than the shockable beat amplitude threshold and the signal width parameter is greater than the shockable beat width threshold.

11. The system of claim 1, wherein the control circuit is further configured to:

increase a count of noisy signal segments in response to each one of the stored time segments being detected as a noisy signal segment;

determine a plurality of intervals between successive ones of the R-waves sensed by the first sensing channel;

determine that a predetermined number of the plurality of intervals are less than a tachyarrhythmia detection interval;

compare a value of the count of noisy signal segments to a rejection threshold in response to detecting the predetermined number of the plurality of intervals being less than the tachyarrhythmia detection interval;

determine that the value of the count of noisy signal segments is equal to or greater than the rejection threshold; and withhold the detection of the tachyarrhythmia episode in response to the value of the count of noisy signal segments being equal to or greater than the rejection threshold.

12. The system of claim 1, wherein the control circuit is configured to:

determine the morphology parameter for a first stored time segment of the stored time segments of the second cardiac electrical signal corresponding to a first sensed R-wave of the plurality of R-waves;

determine that a next sensed R-wave of the plurality of R-waves occurs within a pre-determined time limit from the first sensed R-wave; and skip determining the morphology parameter from a second stored time segment of the stored time segments of the second cardiac electrical signal corresponding to the next sensed R-wave in response to the next sensed R-wave occurring within the pre-determined time limit.

13. The system of claim 1, further comprising an extra-cardiovascular lead, wherein at least one electrode of the first sensing electrode vector is carried by the extra-cardiovascular lead.

14. The system of claim 1, wherein the first sensing electrode vector has a first inter-electrode spacing and the second electrode vector has a second inter-electrode spacing, the second inter-electrode spacing being greater than the first inter-electrode spacing.

15. The system of claim 1, further comprising a therapy delivery circuit configured to deliver an anti-tachyarrhythmia therapy to a patient's heart via electrodes coupled to the medical device system, wherein the control circuit is further configured to:

increase a count of noisy segments in response to each one of the stored time segments being detected as a noisy signal segment;

determine a plurality of intervals between successive ones of the of R-waves sensed by the first sensing channel;

detecting a predetermined number of the plurality of intervals being less than a tachyarrhythmia detection interval;

compare a value of the count of noisy signal segments to a rejection threshold in response to detecting the predetermined number of the plurality of intervals being less than the tachyarrhythmia detection interval;

determining that the value of the count of noisy signal segments is less than the rejection threshold;

detect the tachyarrhythmia episode in response to the value of the count being less than the rejection threshold; and control the therapy delivery circuit to deliver the anti-tachyarrhythmia therapy in response to detecting the tachyarrhythmia episode.

16. A method comprising:

sensing R waves by a first sensing channel of a sensing circuit of a medical device system in response to crossings of a sensing amplitude threshold by a first cardiac electrical signal, the first cardiac electrical signal received by the first sensing channel via a first sensing electrode vector coupled to the medical device system;

storing a time segment of a second cardiac electrical signal in a memory in response to each one of a plurality of R-waves sensed by the first sensing channel from the first cardiac electrical signal, the second cardiac electrical signal received via a second sensing electrode vector coupled to the medical device system, the second sensing electrode vector being different than the first sensing electrode vector;

for each of the stored time segments,
  determining a morphology parameter correlated to signal noise from the stored time segment; and
  detecting the stored time segment as being one of a noisy signal segment or not a noisy signal segment based on the morphology parameter determined for the respective stored time segment;

detecting a threshold number of the stored time segments as noisy signal segments; and withholding detection of a tachyarrhythmia episode in response to detecting at least the threshold number of the stored time segments as noisy signal segments.

17. The method of claim 16, further comprising filtering the time segments of the second cardiac electrical signal by a notch filter prior to determining the morphology parameter.

18. The system of claim 16, further comprising:
determining a plurality of intervals between successive ones of the R-waves sensed by the first sensing channel;
determining that at least a predetermined number of the plurality of intervals are less than a tachyarrhythmia detection interval; and
determining the morphology parameter from each of the stored time segments in response to the predetermined number of the plurality of intervals being less than the tachyarrhythmia detection interval.

19. The method of claim 16, wherein determining the morphology parameter for each of the stored time segments comprises:
identifying signal pulses occurring during the stored time segment of the second cardiac electrical signal; and
determining a count of the identified signal pulses.

20. The method of claim 19, wherein identifying the signal pulses comprises:
identifying zero crossings of the second cardiac electrical signal during the stored time segment; and
determining that the second cardiac electrical signal crosses a noise pulse amplitude threshold between two consecutive zero crossings; and
identifying a signal pulse in response to the second cardiac electrical signal crossing the noise pulse amplitude threshold between two consecutive zero crossings.

21. The method of claim 16, further comprising, for each of the stored time segments:
determining at least one of a signal width parameter or a signal amplitude parameter for the stored time segment;
detecting a potential shockable beat based on at least one of the signal width parameter or the signal amplitude parameter;
comparing the morphology parameter to a first noisy segment threshold in response to detecting the potential shockable beat;
determining that the morphology parameter determined for the stored time segment is greater than or equal to the first noisy segment threshold; and
detecting the stored time segment as a noisy signal segment in response to the morphology parameter determined for the stored time segment being greater than or equal to the first noisy segment threshold.

22. The method of claim 21, further comprising, for each of the stored time segments:
comparing the morphology parameter to a second noisy segment threshold in response to not detecting a potential shockable beat based on the at least one of the signal width parameter or the signal amplitude parameter;
determining that the morphology parameter is greater than or equal to the second noisy segment threshold, the second noisy segment threshold less than the first noisy segment threshold; and
detecting the stored time segment as a noisy signal segment in response to the morphology parameter being greater than or equal to the second noisy segment threshold, the second noisy segment threshold less than the first noisy segment threshold.

23. The method of claim 16, further comprising, for each of the stored time segments:
determining from the stored time segment at least one of a signal width parameter and/or a signal amplitude parameter;
determining that the stored time segment is not a potential shockable beat based on at least one of the signal width parameter and/or the signal amplitude parameter;
comparing the morphology parameter to a noisy segment threshold in response to determining the stored time segment is not a potential shockable beat; and
determining that the stored time segment is a noisy signal segment in response to the morphology parameter determined for the respective stored time segment being greater than or equal to the noisy segment threshold.

24. The method of claim 23, wherein determining the signal width parameter comprises:
identifying zero crossings of the second cardiac electrical signal during the stored time segment;
determining that the second cardiac electrical signal crosses a pulse amplitude threshold between two consecutive zero crossings;
identifying a signal pulse in response to the second cardiac electrical signal crossing the pulse amplitude threshold between two consecutive zero crossings;
determining a pulse width of each identified signal pulse as a time interval between the two consecutive zero crossings of each respective identified signal pulse;
determining the signal width parameter as a maximum one of the determined pulse widths.

25. The method of claim 23, further comprising:
determining the signal amplitude parameter by:

determining a summation of absolute amplitudes of all sample points of the time segment; and normalizing the summation by a maximum sample point amplitude of the time segment;

comparing the signal amplitude parameter to a shockable beat amplitude threshold;

determining that the signal amplitude parameter is greater than the shockable beat amplitude threshold;

comparing the signal width parameter to a shockable beat width threshold;

determining that the signal width parameter is greater than the shockable beat width threshold; and detecting the potential shockable beat when the signal amplitude parameter is greater than the shockable beat amplitude threshold and the signal width parameter is greater than the shockable beat width threshold.

26. The method of claim 16, further comprising:
increasing a count of noisy signal segments in response to each one of the stored time segments being detected as a noisy signal segment;
determining a plurality of intervals between successive ones of the R-waves sensed by the first sensing channel;
determining that a predetermined number of the plurality of intervals are less than a tachyarrhythmia detection interval;
comparing a value of the count of noisy signal segments to a rejection threshold in response to detecting the predetermined number of the plurality of intervals being less than the tachyarrhythmia detection interval;
determining that the value of the count of noisy signal segments is equal to or greater than the rejection threshold; and
withholding the detection of the tachyarrhythmia episode in response to the value of the count of noisy signal segments being equal to or greater than the rejection threshold.

27. The method of claim 16, further comprising:
determining the morphology parameter for a first stored time segment of the stored time segments of the second cardiac electrical signal corresponding to a first sensed R-wave of the plurality of R-waves;
determining that a next sensed R-wave of the plurality of R-waves occurs within a pre-determined time limit from the first sensed R-wave; and
skipping determining the morphology parameter from a second stored time segment of the stored time segments of the second cardiac electrical signal corresponding to the next sensed R-wave in response to the next sensed R-wave occurring within the pre-determined time limit.

28. The method of claim 16, further comprising sensing the first cardiac electrical signal via at least one electrode carried by an extra-cardiovascular lead.

29. The method of claim 16, further comprising:
sensing the first cardiac electrical signal by the first sensing electrode vector having a first inter-electrode spacing; and
sensing the second cardiac electrical signal by the second sensing electrode vector having a second inter-electrode spacing, the second inter-electrode spacing being greater than the first inter-electrode spacing.

30. The method of claim 16, further comprising:
increasing a count of noisy segments in response to each one of the stored time segments being detected as a noisy signal segment;
determining a plurality of intervals between successive ones of the of R-waves sensed by the first sensing channel;
detecting a predetermined number of the plurality of intervals being less than a tachyarrhythmia detection interval;
comparing a value of the count of noisy signal segments to a rejection threshold in response to detecting the predetermined number of the plurality of intervals being less than the tachyarrhythmia detection interval;
determining that the value of the count of noisy signal segments is less than the rejection threshold;
detecting the tachyarrhythmia episode in response to the value of the count being less than the rejection threshold; and
controlling a therapy delivery circuit of the medical device system to deliver an anti-tachyarrhythmia therapy in response to detecting the tachyarrhythmia episode.

31. A non-transitory, computer-readable storage medium comprising a set of instructions which, when executed by a control circuit of an extra-cardiovascular implantable cardioverter defibrillator (ICD), cause the extra-cardiovascular ICD to:
sense a plurality of R-waves by a first sensing channel of a sensing circuit of the extra-cardiovascular ICD in response to crossings of a sensing amplitude threshold by a first cardiac electrical signal, the first cardiac electrical signal received by the first sensing channel via a first extra-cardiovascular sensing electrode vector coupled to the extra-cardiovascular ICD;
store a time segment of a second cardiac electrical signal in ICD memory in response to each one of the plurality of R-waves sensed by the first sensing channel, the second cardiac electrical signal received via a second extra-cardiovascular sensing electrode vector by a second sensing channel of the extra-cardiovascular ICD, the second extra-cardiovascular sensing electrode vector different than the first extra-cardiovascular sensing electrode vector;
for each one of the stored time segments:
determine a morphology parameter correlated to signal noise from the stored time segment; and
detect the stored time segment as being one of a noisy signal segment or not a noisy signal segment based on the morphology parameter determined for the respective stored time segment;
detect a threshold number of the stored time segments as noisy signal segments; and
withhold detection of a tachyarrhythmia episode in response to detecting at least the threshold number of the stored time segments as noisy signal segments.

* * * * *